United States Patent
Smith et al.

(10) Patent No.: US 9,060,847 B2
(45) Date of Patent: Jun. 23, 2015

(54) OPTICAL HYDROGEL MATERIAL WITH PHOTOSENSITIZER AND METHOD FOR MODIFYING THE REFRACTIVE INDEX

(75) Inventors: Thomas Smith, Penfield, NY (US); Wayne H. Knox, Pittsford, NY (US); Li Ding, Rochester, NY (US); Dharmendra Jani, Fairport, NY (US); Jeffrey G. Linhardt, Fairport, NY (US)

(73) Assignees: University of Rochester, Rochester, NY (US); Rochester Institute of Technology, Rochester, NY (US)

( * ) Notice: Subject to any disclaimer, the term of this patent is extended or adjusted under 35 U.S.C. 154(b) by 661 days.

(21) Appl. No.: 12/380,892

(22) Filed: Mar. 4, 2009

(65) Prior Publication Data

US 2009/0287306 A1    Nov. 19, 2009

Related U.S. Application Data

(60) Provisional application No. 61/054,225, filed on May 19, 2008.

(51) Int. Cl.
*B05D 3/06* (2006.01)
*A61L 27/50* (2006.01)
(Continued)

(52) U.S. Cl.
CPC .......... *A61F 9/00804* (2013.01); *A61F 2/1627* (2013.01); *A61F 2/1635* (2013.01);
(Continued)

(58) Field of Classification Search
USPC .............. 264/1.37; 623/6.11, 6.57, 6.16, 6.56
See application file for complete search history.

(56) References Cited

U.S. PATENT DOCUMENTS 2,725,377 A * 11/1955 Long et al. .................... 534/802
3,959,281 A *  5/1976 Beyerle et al. ................ 544/376
(Continued)

FOREIGN PATENT DOCUMENTS

DE    102005045540 A1 *  3/2007
EP       0575885 A1      12/1993
(Continued)

OTHER PUBLICATIONS

Polymers for in vivo Tuning of Refractive Properties in Intraocular Lenses, Trager et. al., Macromolecular Bioscience, vol. 8, Issue 2, Article first published online Oct. 19, 2007, pp. 177-183.*
(Continued)

*Primary Examiner* — James J Seidleck
*Assistant Examiner* — Peter A Salamon
(74) *Attorney, Agent, or Firm* — Andrew J. Anderson, Esq.; Harter Secrest & Emery LLP

(57) ABSTRACT

A method for modifying the refractive index of an optical, hydrogel polymeric material. The method comprises irradiating predetermined regions of an optical, polymeric material with a laser to form refractive structures. To facilitate the formation of the refractive structures the optical, hydrogel polymeric material comprises a photosensitizer. The presence of the photosensitizer permits one to set a scan rate to a value that is at least fifty times greater than a scan rate without the photosensitizer in the material, yet provides similar refractive structures in terms of the observed change in refractive index. Alternatively, the photosensitizer in the polymeric material permits one to set an average laser power to a value that is at least two times less than an average laser power without the photosensitizer in the material, yet provide similar refractive structures.

16 Claims, 17 Drawing Sheets

(51) Int. Cl.
*A61L 27/52* (2006.01)
*A61F 9/008* (2006.01)
*B29D 11/00* (2006.01)
*A61F 2/16* (2006.01)

(52) U.S. Cl.
CPC ............ *A61L 27/50* (2013.01); *A61L 27/52* (2013.01); *A61L 2430/16* (2013.01); *G02C 2202/14* (2013.01); *B29D 11/00009* (2013.01)

(56) References Cited

U.S. PATENT DOCUMENTS

| | | | |
|---|---|---|---|
| 4,907,586 A | 3/1990 | Bille et al. | |
| 5,220,359 A | 6/1993 | Roffman | |
| 5,849,006 A | 12/1998 | Frey et al. | |
| 5,964,748 A | 10/1999 | Peyman | |
| 6,197,057 B1 | 3/2001 | Peyman et al. | |
| 6,261,220 B1 | 7/2001 | Frey et al. | |
| 6,270,221 B1 | 8/2001 | Liang et al. | |
| 6,271,914 B1 | 8/2001 | Frey et al. | |
| 6,450,642 B1 | 9/2002 | Jethmalani et al. | |
| 6,489,589 B1 | 12/2002 | Alexander | |
| 6,710,097 B2 * | 3/2004 | Takase et al. | 522/97 |
| 6,770,728 B2 | 8/2004 | Watanabe et al. | |
| 6,849,671 B2 | 2/2005 | Steffen et al. | |
| 6,857,744 B2 | 2/2005 | Nakada et al. | |
| 6,887,269 B1 * | 5/2005 | Hampp et al. | 623/6.57 |
| 7,037,954 B2 | 5/2006 | Baba et al. | |
| 7,074,840 B2 * | 7/2006 | Chang et al. | 522/65 |
| 7,085,469 B2 | 8/2006 | Mune et al. | |
| 7,105,110 B2 | 9/2006 | Platt et al. | |
| 2002/0048726 A1 * | 4/2002 | Kikkawa et al. | 430/283.1 |
| 2002/0100990 A1 | 8/2002 | Platt et al. | |
| 2003/0049850 A1 * | 3/2003 | Golden | 436/56 |
| 2003/0052311 A1 | 3/2003 | Inagaki et al. | |
| 2004/0015236 A1 | 1/2004 | Sarfarazi | |
| 2004/0206940 A1 * | 10/2004 | Boschetti et al. | 252/500 |
| 2004/0238977 A1 | 12/2004 | Ilyashenko | |
| 2004/0243111 A1 | 12/2004 | Bendett et al. | |
| 2004/0265737 A1 | 12/2004 | Hanamura et al. | |
| 2005/0018130 A1 | 1/2005 | Dahi et al. | |
| 2005/0027031 A1 * | 2/2005 | Chang et al. | 522/68 |
| 2005/0116207 A1 | 6/2005 | Tani | |
| 2005/0187622 A1 | 8/2005 | Sandstedt et al. | |
| 2005/0192563 A1 | 9/2005 | Platt et al. | |
| 2005/0195361 A1 | 9/2005 | Jethmalani et al. | |
| 2006/0017990 A1 | 1/2006 | Platt et al. | |
| 2006/0083890 A1 | 4/2006 | Takizawa | |
| 2006/0106126 A1 | 5/2006 | Chang et al. | |
| 2006/0135952 A1 | 6/2006 | Curatu et al. | |
| 2007/0172905 A1 * | 7/2007 | Taran et al. | 435/7.92 |
| 2008/0001320 A1 * | 1/2008 | Knox et al. | 264/1.37 |
| 2009/0143858 A1 | 6/2009 | Knox et al. | |
| 2009/0157178 A1 * | 6/2009 | Hampp | 623/6.11 |
| 2011/0245919 A1 * | 10/2011 | Pettit | 623/6.22 |

FOREIGN PATENT DOCUMENTS

| | | |
|---|---|---|
| EP | 1234655 A1 | 8/2002 |
| EP | 1703313 A1 | 9/2006 |
| JP | 2001147301 | 5/2001 |
| WO | WO 00/41650 A1 | 7/2000 |
| WO | WO 01/71411 A2 | 9/2001 |
| WO | WO 2004/006794 A1 | 1/2004 |
| WO | WO 2005/015268 A2 | 2/2005 |
| WO | WO 2005015268 A2 * | 2/2005 |
| WO | WO 2006/002201 A2 | 1/2006 |
| WO | WO 2006/112952 A2 | 10/2006 |
| WO | 2007137102 A2 | 11/2007 |
| WO | WO 2008/002796 A2 | 1/2008 |

OTHER PUBLICATIONS

International Preliminary Examining Authority, "International Preliminary Report on Patentability," PCT/US2007/071538, (Nov. 21, 2008).

Ding et al., "Micro-Raman spectroscopy of refractive index microstructures in silicone-based hydrogel polymers created by high-repetition-rate femtosecond laser micromachining," J Opt Soc Am B, Apr. 2009, (vol. 26), (Issue. 4), (p. 595-602).

Ding et al., "Large refractive index change in silicone-based and non-silicone-based hydrogel polymers induced by femtosecond laser micro-machining," Optics Express, (vol. 14), (Issue. 24), (p. 11901-11909), (Nov. 27, 2006).

Eaton et al., "Heat accumulation effects in femtosecond laser-written waveguides with variable repetition rate," Optics Express, (vol. 13), (Issue. 12), (p. 4708-4716), (Jun. 13, 2005).

Menon et al., "Zone-plate-array lithograph (ZPAL): Optical maskless lithography for cost-effective patterning," Proc SPIE, May 2005, (p. 330-339).

Menon et al., "Maskless lithography," Materialstoday, Feb. 2005, (p. 26-33).

Oshika et al., "Three year prospective, randomized evaluation of intraocular lens implantatior through 3.2 and 5.5 mm incisions," J Cat Refr Surg, Apr. 1998, (vol. 24), (p. 509-514).

Kim et al., "Two-Photon Triggered Drug Delivery System: A New Way to Prevent Posterior Capsule Opacification," Oph. Tech. XVI, 2006, vol. 6138, (p. S1-S7).

Leise et al., "1,1-Dimethylnaphthalenon-dimers as Photocleavable Linkers with Improved Two-Photon-Absorption Efficiency and Hydrolytic Stability," J. of Photochem. and Photobiol. A, 2010, (vol. 209), (p. 128-134).

Trager et al., "Two-Photon Treatment," Nature Photonics, Sep. 2007, (vol. 1), (p. 509-511).

Trager et al., "Two-Photon-Induced Cycloreversion Reaction of Chalcone Photodimers," Chem. Phys. Lett., 2008, (vol. 455), (p. 307-310).

* cited by examiner

OPTICAL HYDROGEL MATERIAL WITH PHOTOSENSITIZER AND METHOD FOR MODIFYING THE REFRACTIVE INDEX

The application claims the benefit of U.S. provisional application no. 61/054,225 filed May 19, 2008 under 35 U.S.C. §119(e).

The present invention relates to a method of using a laser to modify the refractive index of an optical device that includes an optical, hydrogel polymeric material, and the resulting optical device.

BACKGROUND OF THE INVENTION

In general, there are two types of intraocular lenses. One type replaces the eye's natural lens, usually to replace a cataractous lens. The other type is used to supplement an existing lens and functions as a permanent corrective lens. This type of lens (referred to as a phakic IOL) is implanted in the anterior or posterior chamber to correct refractive errors of the eye. The power of the lens, i.e., point focus on the retina from light originating at infinity, to be implanted is determined based on pre-operative measurements of ocular length and corneal curvature of each patient. The pre-operative measurements are conducted with the hope that the patient will need little, if any, vision correction following the surgery. Unfortunately, due to errors in measurement, variable lens positioning or wound healing, most patients undergoing cataract surgery will not enjoy optimal vision without some form of vision correction following the surgery. Brandser et al., *Acta. Opthalmol. Scand.* 75:162 165 (1997); Oshika et al., *J. Cataract Refract. Surg.* 24:509 514 (1998). In-part because the power of present IOLs is fixed and cannot be adjusted post-implantation most patients must use corrective lenses such as eye glasses or contact lenses following surgery.

One potential alternative to post-operative, corrective lenses is a light-adjustable intraocular lens whose refractive properties can be modified following insertion of the lens into a human eye. Such a lens is reported in U.S. Pat. No. 6,450,642, hereafter referred to as the Calhoun Patent. The light-adjustable lens is said to comprise (i) a first polymer matrix and (ii) a refraction modulating composition (RMC) that is capable of stimulus-induced polymerization. As stated, when a portion of the described lens is exposed to light of sufficient intensity, the RMC forms a second polymer matrix. The process is said to result in a light adjusted, power-modified lens.

As described in the Calhoun Patent, the first polymer matrix and the RMC are selected such that the components that comprise the RMC are capable of diffusion within the first polymer matrix. Put another way, a loose first polymer matrix will tend to be paired with larger RMC components and a tight first polymer matrix will tend to be paired with smaller RMC components. Upon exposure to an appropriate energy source (e.g., heat or light), the RMC typically forms a second polymer matrix in the exposed region of the optical element. After exposure, the RMC in the unexposed region will migrate into the exposed region over time. The amount of RMC migration into the exposed region is said to be time dependent and controllable. If enough time is permitted, the RMC components will re-equilibrate and redistribute throughout the lens material (i.e., the first polymer matrix, including the exposed region). When the region is re-exposed to the energy source, the RMC that has since migrated into the region polymerizes to further increase the formation of the second polymer matrix. This process (exposure followed by an appropriate time interval to allow for diffusion) may be repeated until the exposed region of the optical element has reached the desired property (e.g., power, refractive index, or shape). The entire optical element is then exposed to an energy source to "lock-in" the desired lens property by polymerizing the remaining RMC in the lens material. Overall, the power of the lens is changed by a shape change caused by the migration of the RMC and subsequent polymerization(s).

U.S. Pat. No. 7,105,110 describes a method and instrument to irradiate a light adjustable lens as described in the Calhoun Patent with an appropriate amount of radiation in an appropriate pattern. The method is said to include aligning a source of the modifying radiation so as to impinge the radiation onto the lens in a pattern, and controlling the quantity of the impinging radiation. The quantity of the impinging radiation is controlled by controlling the intensity and duration of the irradiation.

There exists an ongoing need for new materials and processes to improve a patient's vision following cataract surgery. Accordingly, there is a need for an optical device, e.g., an IOL, whose refractive power can be modified by a change in the refractive index of a lens material post-operative implantation.

There is also interest in the ophthalmic community for an IOL that provides a patient with an extended depth of field or with a multifocal modality to improve a patient's visual acuity at variable distances.

SUMMARY OF THE INVENTION

The invention is directed to a method for modifying the refractive index of an optical, hydrogel polymeric material. The method comprises irradiating predetermined regions of the optical, hydrogel polymeric material with a laser to form refractive structures. The refractive structures are characterized by a change in the refractive index of the hydrogel polymeric material. To facilitate the formation of the refractive structures the optical, hydrogel polymeric material comprises a photosensitizer. The presence of the photosensitizer permits one to set a scan rate to a value that is at least fifty times greater than a scan rate without the photosensitizer in the material, yet provides similar refractive structures in terms of the observed change in refractive index. Alternatively, the photosensitizer in the polymeric material permits one to set an average laser power to a value that is at least two times less than an average laser power without the photosensitizer in the material, yet provide similar refractive structures.

The invention is also directed to an optical device comprising an optical, hydrogel polymeric material with predetermined regions that have been irradiated with a laser to form refractive structures. To facilitate the formation of the refractive structures the optical, hydrogel polymeric material comprises a photosensitizer. The presence of the photosensitizer permits one to set a scan rate to a value that is at least fifty times greater than a scan rate without the photosensitizer in the material, yet provides similar refractive structures in terms of the observed change in refractive index. Alternatively, the photosensitizer in the polymeric material permits one to set an average laser power to a value that is at least two times less than an average laser power without the photosensitizer in the material, yet provide similar refractive structures.

The invention is also directed to a method for modifying the refractive index of an intraocular tens following the surgical insertion of the lens in a human eye. The intraocular lens will include an optical, hydrogel polymeric material. The method comprises instructing a surgeon to identify and measure optical aberrations, or to evaluate the need for vision correction, in the lens following the surgical procedure, and to determine the position and shape of refractive structures to be formed within the hydrogel, polymeric material to correct for the aberrations or to optimize the patient's vision. The method also includes irradiating predetermined regions of the hydrogel, polymeric material with a laser to form the refractive structures. To facilitate the formation of the refractive structures the optical, hydrogel polymeric material comprises a photosensitizer. The presence of the photosensitizer permits one to set a scan rate to a value that is at least fifty times greater than a scan rate without the photosensitizer in the material, yet provides similar refractive structures in terms of the observed change in refractive index. Alternatively, the photosensitizer in the polymeric material permits one to set an average laser power to a value that is at least two times less than an average laser power without the photosensitizer in the material, yet provide similar refractive structures.

The invention is also directed to a method for modifying the refractive index of an intraocular lens prior to the surgical insertion of the lens in a human eye. In this case, the described irradiation process is used in a manufacturing environment to create refractive structures in the intraocular lens. The refractive structures can be designed to enhance the depth of field of the lens or create select regions of variable power to custom fit the lens to the needs of a particular patient. Alternatively, the refractive structures can be designed to create a multifocal lens.

BRIEF DESCRIPTION OF THE DRAWINGS

The invention will be better understood from the following description and in consideration with the accompanying figures. It is to be expressly understood, however, that each of the figures is provided to further illustrate and describe the invention and is not intended to further limit the invention claimed.

DETAILED DESCRIPTION OF THE INVENTION

Figure 1A:
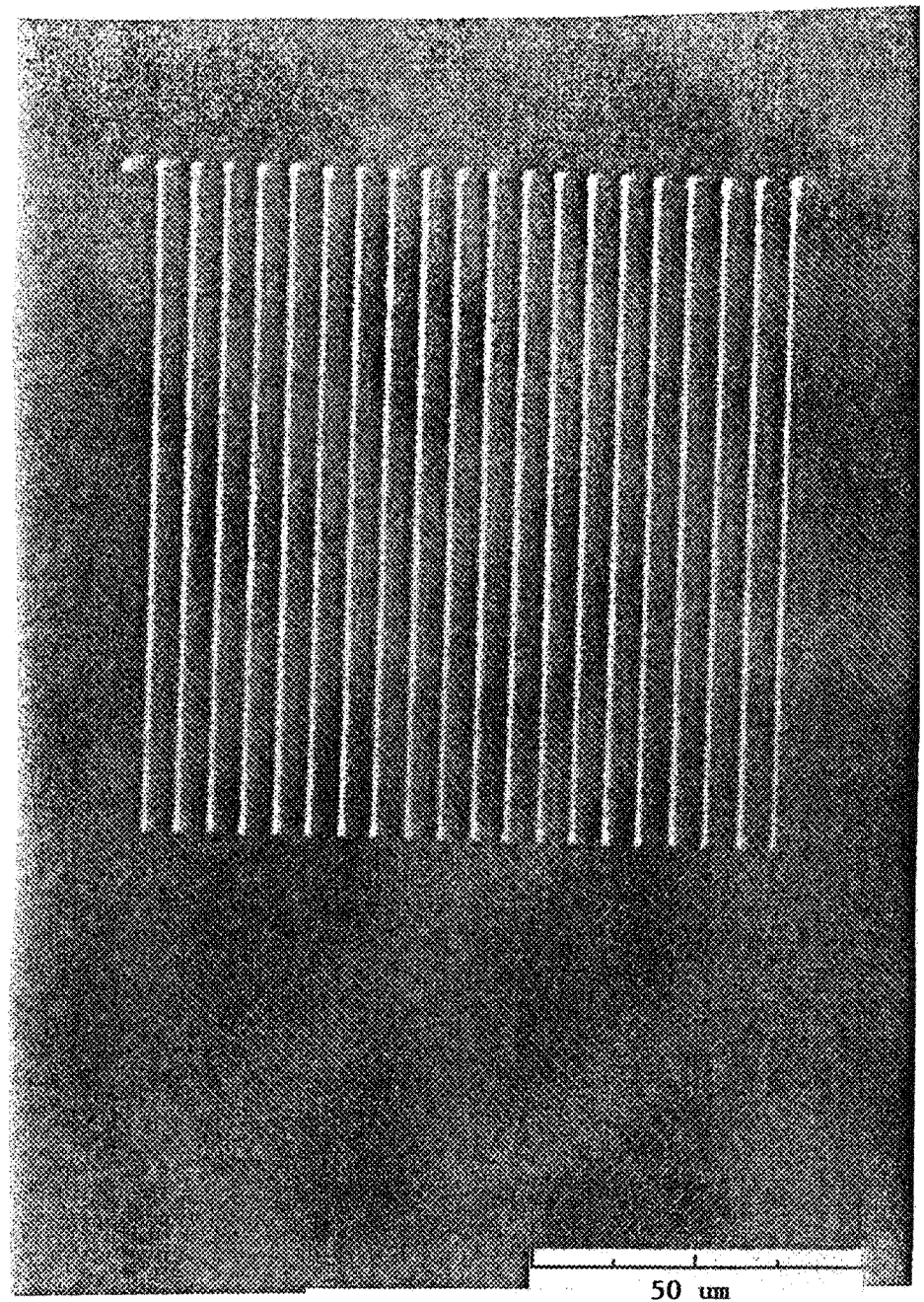
FIG. 1A is a microscope photograph of a line grating written in an optical, polymeric material produced by laser irradiation.

If very short laser pulses of sufficient energy are used to irradiate an optical, hydrogel polymeric material, the intensity of light within the focal volume causes a nonlinear absorption of photons (typically multi-photon absorption) and leads to a change in the refractive index of the material within the focal volume. Moreover, portions of the material just outside the focal volume is minimally affected by the laser light. The femtosecond laser pulse sequence used in the experiments operates at a high repetition-rate, e.g., 80 MHz, and consequently the thermal diffusion time (>0.1 μs) is much longer than the time interval between adjacent laser pulses (~11 ns). Under such conditions, absorbed laser energy can accumulate within the focal volume and increase the local temperature. We believe that this thermal mechanism likely plays a role in the formation of laser-induced refractive structures in optical, hydrogel polymeric materials. The presence of water in the polymeric material is very important, and is believed to profoundly influence the formation of the refractive structures.

Accordingly, the invention is directed to a method for modifying the refractive index of an optical, hydrogel polymeric material that comprises a photosensitizer. The method comprises irradiating select regions of the optical, hydrogel polymeric material with a laser. The irradiated regions exhibit little or no scattering loss, which means that the resulting refractive structures that form in the focal volume are not clearly visible under appropriate magnification without phase contrast enhancement. In other words, the refractive structures are virtually transparent to the human eye without some form of image enhancement.

To facilitate the formation of the refractive structures, the optical, hydrogel polymeric material comprises a photosensitizer. The presence of the photosensitizer permits one to set a scan rate to a value that is at least fifty times greater, or at least 100 times greater, than a scan rate without the photosensitizer present in the material, and yet provide similar refractive structures in terms of the observed change in refractive index of the material in the focal volume. Alternatively, the photosensitizer in the polymeric material permits one to set an average laser power to a value that is at least two times less, preferably four times less, than an average laser power without the photosensitizer in the material, yet provide similar refractive structures. Simply stated, it is believed that a photosensitizer having a greater multi-photon absorption cross section captures the light radiation (photons) with greater efficiency and then transfers that energy to the optical, hydrogel polymeric material within the focal volume. The transferred energy then leads to the formation of the refractive structures and the observed change in the refractive index of the material in the focal volume.

To date, we have used a 60× 0.70NA Olympus LUCPlanFLN long-working-distance microscope objective with variable spherical aberration compensation. As indicated by the following equation $$\Delta T(r, z, t=0) = \frac{\beta \tau_p [I(0,0)]^2 \exp\left[-4\left(\frac{r^2}{a^2} + \frac{z^2}{b^2}\right)\right]}{c_p \rho}$$

the localized instantaneous temperature depends on both the pulse intensity and the magnitude of the TPA coefficient. In order to produce an optical modification of a material that is of purely refractive character, i.e. not absorbing or scattering, then it is imperative to avoid optical damage, i.e., observed burning (scorching) or carbonization of the polymeric material. Such material or optical damage can be caused by excitation intensities exceeding a critical free-electron density. For hydrogel polymers containing a fair amount of water, the optical breakdown threshold is much lower than that in silica glasses. This breakdown threshold limits the pulse energy (in many cases, to approximately 0.1 nJ to 10 nJ) that the hydrogel polymers can tolerate, and yet provide the observed changes in the refractive index within the focal volume. The irradiation process and conditions described herein are very different from what has been reported in femtosecond laser micromachining studies in silica in which much larger pulse energies and much larger temperature increase (several thousand Kelvin) have been observed. See, S. M. Eaton et al. in "*Heat accumulation effects in femtosecond laser-written waveguides with variable repetition rate,*" Opt. Express 2005, 13, 4708-16. Also, the specific heat constant $C_p$ of water is much larger than that of silica glass ($C_p$=8.40 JK$^{-1}$kg$^{-1}$), and therefore the presence of water in the hydrogel polymeric material is believed to moderate the temperature increase in the focal volume.

Another way to increase energy absorption at a given intensity level is to increase the nonlinear absorption coefficient β by doping the optical, hydrogel polymeric material with a particular chromophore and tuning the short pulse laser near a two-photon transition of the chromophore.

In this regard, we have prepared optical, hydrogel materials doped with a non-polymerizable chromophore or a polymerizable chromophore. In the former case of a nonpolymerizble chromophore, we prepared solutions containing the chromophore and allowed the optical, hydrogel polymeric materials to come in contact with such solutions to allow up-take of the chromophore into the polymeric matrix of the polymer. In the later case of a polymerizble chromophore, we used monomers containing a chromophore, e.g., a fluoresceinbased monomer, in the monomer mixture such that the chromophore becomes part of the polymeric matrix.

Of course, one of ordinary skill would recognize that one could easily use a solution containing a non-polymerizable chromophore to dope an optical, hydrogel polymeric material that had been prepared with a polymerizable chromophore. Also, it is to be understood that the chromophoric entities could be the same or different.

Our studies have shown that by doping the hydrogel material with the photosensitizer either by solution doping or by using a polymerizable chromophore the localized temperature increase can reach a transition point of the polymer. The goal being to reach this transition point to provide a desired change in the refraction index, yet maintain a safe margin of intensity below the damage threshold level of the hydrogel material.

Due to the high repetition rate pulse sequence we use in the irradiation process, the accumulated focal temperature increase can be much larger than the temperature increase induced by a single laser pulse. The accumulated temperature increases until the absorbed power and the dissipated power are in dynamic balance. For hydrogel polymers, thermal-induced additional cross-linking within the polymer network can produce a change in the refractive index as the local temperature exceeds a transition temperature. If the temperature increase exceeds a second threshold, a somewhat higher temperature than the transition temperature, the polymer is pyrolytically degraded, and carbonized residue and water bubbles are observed. In other words, the material exhibits visible optical damage (scorching)—like scorching or burning holes in a piece of paper with a magnifying glass on a sunny day. As a result from our investigations described herein, each of the following experimental parameters such as laser repetition-rate, laser wavelength and pulse energy, TPA coefficient and water concentration of the materials should be considered so that a desired change in the refractive index can be induced in the hydrogel polymers without optical damage.

The pulse energy and the average power of the laser, and the rate at which the irradiated regions are scanned, will in-part depend on the type of hydrogel polymeric material that is being irradiated, how much of a change in refractive index is desired and the type of refractive structures one wants to imprint within the material. The selected pulse energy will also depend upon the scan rate and the average power of the laser at which the structures are written into the hydrogel material. Typically, greater pulse energies will be needed for greater scan rates and lower laser power. For example, some materials will call for a pulse energy from 0.05 nJ to 100 nJ or from 0.2 nJ to 10 nJ.

Within the stated pulse energies above, the optical, hydrogel polymeric material is irradiated at a scan rate of at least 0.1 mm/s, from 0.1 mm/s to 10 mm/s or from 0.4 mm/s to 4 mm/s.

Within the stated pulse energies and scan rates above, the average laser power used in the irradiation process is from 10 mW to 400 mW, or from 40 mW to 220 mW.

In one embodiment, the average pulse energy is from 0.2 nJ to 10 nJ and the average laser power is from 40 mW to 220 mW. The laser also operates within a wavelength of 650 nm to 950 nm. Within the stated laser operating powers, the optical, hydrogel polymeric material is irradiated at a scan rate from 0.4 mm/s to 4 mm/s.

A photosensitizer is a chromophore in which there is no intrinsic linear absorption in the spectra range of 600-1000 nm. The photosensitizer is present in the optical, hydrogel polymeric material to enhance the photoeffiency of the two photon absorption required for the formation of the described refractive structures. Photosensitizers of particular interest include, but are not limited to, the following compounds. The compounds below are merely exemplary.

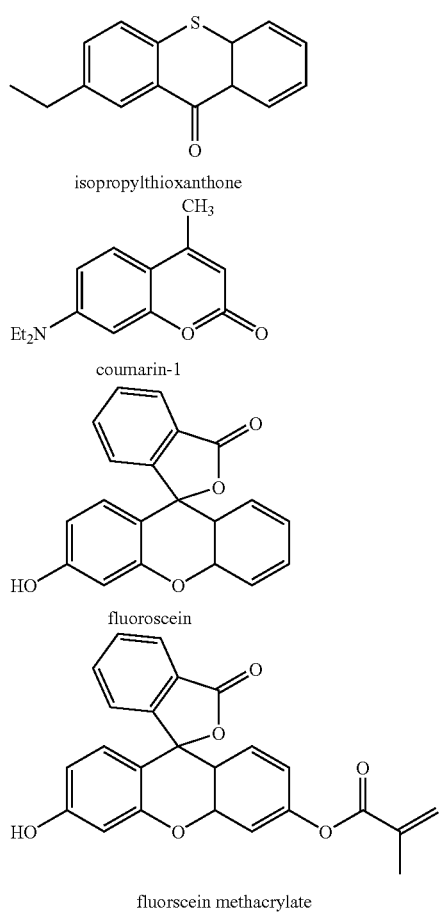

isopropylthioxanthone coumarin-1 fluoroscein fluorscein methacrylate

As is described in greater detail in the Example section, a commercial IOL material, Akreos®, presently marketed by Bausch & Lomb, was subjected to laser irradiation according to the processes described herein. The micromachining process was used to imprint refractive structures in an Akreos® IOL without photosensitizer and an Akreos® IOL doped with a solution containing 17 wt. % cormarin-1. The irradiation experiments were conducted with both dry and hydrated materials. The refractive structures formed only in the hydrated materials.

In brief, the magnitude of the measured change in refractive index was at least ten times greater in the Akreos® IOL doped with the coumarin solution at a given scan rate and an average laser power than the Akreos® IOL without the coumarin. Surprisingly, an increase in scan rate to 1 mm/s at an average laser power of 160 mW provided refractive structures (a line grating) with a change in refractive index of 0.02 to 0.03. Moreover, reducing the laser power to 60 mW still provided refractive structures with a change in refractive index of about 0.005.

In another embodiment, a balafilcon A silicone hydrogel was prepared by adding fluorescein monomer (0.17% by weight) to the polymer monomer mixture. The balafilcon A doped with fluorescein was then subjected to laser radiation according to the processes described herein. Again, the described irradiation process was used to imprint refractive structure in the silicone hydrogel without photosensitizer and the silicone hydrogel doped with 0.17 wt. % fluorescein. Again, experiments were conducted with both dry and hydrated materials, and again, the refractive structures formed only in the hydrated materials.

In brief, the magnitude of the measured change in refractive index was at least ten times greater in the balafilcon A silicone hydrogel doped with 0.17 wt. % fluorescein at an average laser power of 60 mW than balafilcon A without the photosensitizer. This 10-fold difference in change in refractive index was observed even with a 10-fold increase in scan rate in the photosensitized material—0.5 μm/s in the undoped material and 5.0 μm/s in the photosensitized material.

In some cases, the formation of refractive structures as described requires that the pulse width be preserved so that the pulse peak power is strong enough to exceed the nonlinear absorption threshold of the optical, hydrogel polymeric material. However, the glass of the focusing objective(s) significantly increases the pulse width due to the positive dispersion of the glass. A compensation scheme is used to provide a corresponding negative dispersion that can compensate for the positive dispersion introduced by the focusing objective(s). Accordingly, a compensation scheme can be used to correct for the positive dispersion introduced by the focusing objective(s). The compensation scheme can include an optical arrangement selected from the group consisting of at least two prisms and at least one mirror, at least two diffraction gratings, a chirped mirror and dispersion compensating mirrors to compensate for the positive dispersion introduced by the focus objective.

In one embodiment, the compensation scheme comprises at least one prism, in many cases at least two prisms, and at least one mirror to compensate for the positive dispersion of the focusing objective. In another embodiment, the compensation scheme comprises at least two gratings to compensate for the positive dispersion of the focusing objective. Any combination of prisms, gratings and/or mirrors can be used for the compensation scheme.

The laser will generate light with a wavelength in the range from violet to near-infrared radiation. In various embodiments, the wavelength of the laser is in the range from 400 nm to 1500 nm, from 400 nm to 1200 nm or from 600 nm to 900 nm.

In one particular embodiment, the laser is a pumped Ti:sapphire laser with an average power of 10 mW to 1000 mW. Such a laser system will generate light with a wavelength of approximately 800 nm. In another embodiment, an amplified fiber laser that can generate light with a wavelength from 1000 nm to 1600 nm can be used.

The laser will have a peak intensity at focus of greater than 1013 W/cm2. At times, it may be advantageous to provide a laser with a peak intensity at focus of greater than 1014 W/cm2, or greater than 1015 W/cm2.

The ability to form refractive structures in optical, hydrogel polymeric materials provides an important opportunity to an ocular surgeon to modify the refractive index of an optical device, e.g., an intraocular lens or corneal inlay, following implantation of the device into an eye of a patient. The method allows the surgeon to correct any aberrations as a result of the surgery. The method also allows the surgeon to adjust the refractive properties of the lens or inlay by adjusting the refractive index in the irradiated regions based on the vision correction of each patient. For example, starting from a lens of selected power (will vary according to the ocular requirements of the patient), the surgeon can further adjust the refractive properties of the lens to correct a patients vision based upon the individual needs of the patient. In essence, an intraocular lens would essentially function like contact lenses or glasses to individually correct for the refractive error of a patient's eye. Moreover, because the implanted lens can be adjusted by adjusting the refractive index of select regions of the lens, post-operative refractive errors resulting from pre-operative measurement errors, variable lens positioning during implantation and wound healing (aberrations) can be corrected or fine tuned in-situ.

For instance, cataract surgery typically requires that the natural lens of each eye be replaced with an intraocular lens (IOL). Following insertion of the IOL the surgeon can correct for aberrations resulting from the surgery or correct for slight misplacement of the IOL. Following surgery, and after allowing time for the wound to heal, the patient would return to the surgeon to have select regions of the IOL irradiated. These irradiated regions would experience a positive change in refractive index, which would correct for the aberrations as well as the patients needs for vision correction. In some instances, the surgeon would be able to adjust the IOL in one eye for distance and adjust the IOL in the opposite eye for reading.

Typically, the irradiated portions of the optical, hydrogel polymeric material will exhibit a positive change in refractive index of about 0.01 or more. In one embodiment, the refractive index of the region will increase by about 0.03 or more. In fact, applicants have measured a positive change in refractive index in a hydrated, Akreos® IOL material of about 0.06.

It is to be understood by one of ordinary skill in the art, that the method described herein modifies the refractive properties of the material not by casting an optical material with nonreacted monomer (refraction modulation composition) followed by laser irradiation to promote additional polymerization chemistry as described in the Calhoun Patent, but rather by a change in the refractive index of an already completely polymerized optical material. The term "completely polymerized" when used to characterize the optical materials used in the method means that the optical materials are 95% or more polymerized. One way to measure the completeness of a polymerized optical material is by near infra-red spectroscopy, which is used to qualitatively determine the vinyl content of the material. Simple gravimetric weight analysis can also be used.

The irradiated regions of the optical, hydrogel polymeric material can be defined by two- or three-dimensional structures. The two- or three-dimensional structures can comprise an array of discrete cylinders. Alternatively, the two- or three-dimensional structures can comprise a series of lines (a grating) or a combination of an array of cylinders and a series of lines. Moreover, the two- or three-dimensional structures can comprise area or volume filled structures, respectively. These area or volume filled structures are formed by continuously scanning the laser over a select region of the polymeric material.

Nanometer-sized structures can also be formed by the zone-plate-array lithography method describe by R. Menon et al., *Proc. SPIE*, Vol. 5751, 330-339 (May 2005); *Materials Today*, p. 26 (February 2005).

In one embodiment, the irradiated regions of the optical device are defined by a series of lines in a two dimensional plane having a width from 0.2 µm to 3 µm, preferably a width from 0.6 µm to 1.5 µm and a height from 0.4 µm to 8 µm, preferably a height from 1.0 µm to 4 µm (height is measured in the z direction of the material, which is parallel to direction of the laser light). For example, one can generate a line grating comprising a plurality of lines with each line of any desired length, about 0.8 µm to about 1.5 µm in width and about 2 µm to 5 µm in height. The lines can be separated by as little as 1.0 µm (0.5 µm spacing), and any number of lines can be incorporated into the material. Moreover, the grating can be positioned at any selected depth (z-direction), and any number of line gratings can be generated at various depths into the material.

Figure 1B:
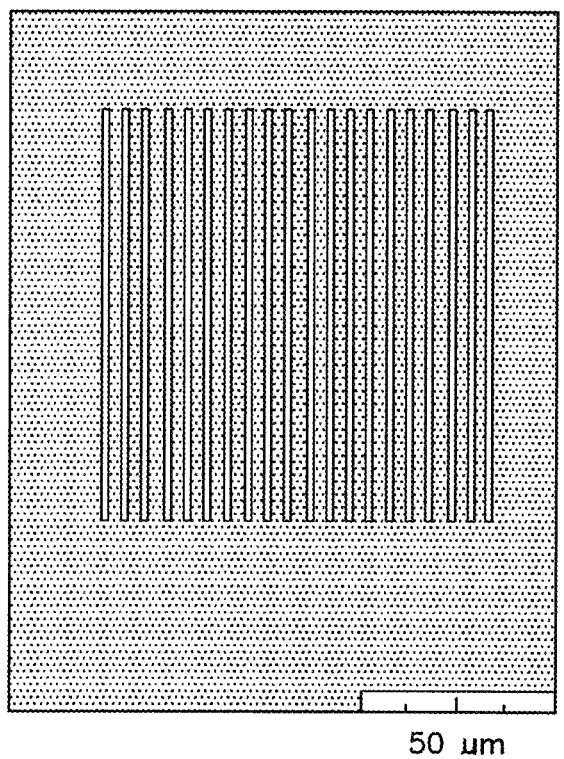
FIG. 1B is a schematic representation of the microscope photograph of FIG. 1A.

FIG. 1A is a microscope photograph with contrasting background of a line grating comprising 20 lines written into an optical material. FIG. 1B is a schematic representation of the microscope photograph of FIG. 1A. Each line is about 100 µm in length, about 1 µm in width with a line separation of about 5 µm. The lines have a height of about 3 µm and were written into the material at a distance of about 100 µm from the top surface of the material. Similar microscope photographs exhibiting line gratings were obtained at a distance of about 200 µm and 400 µm from the top surface of the material, thereby demonstrating that structures can be written into the optical material at any selected depth.

Figure 2A:
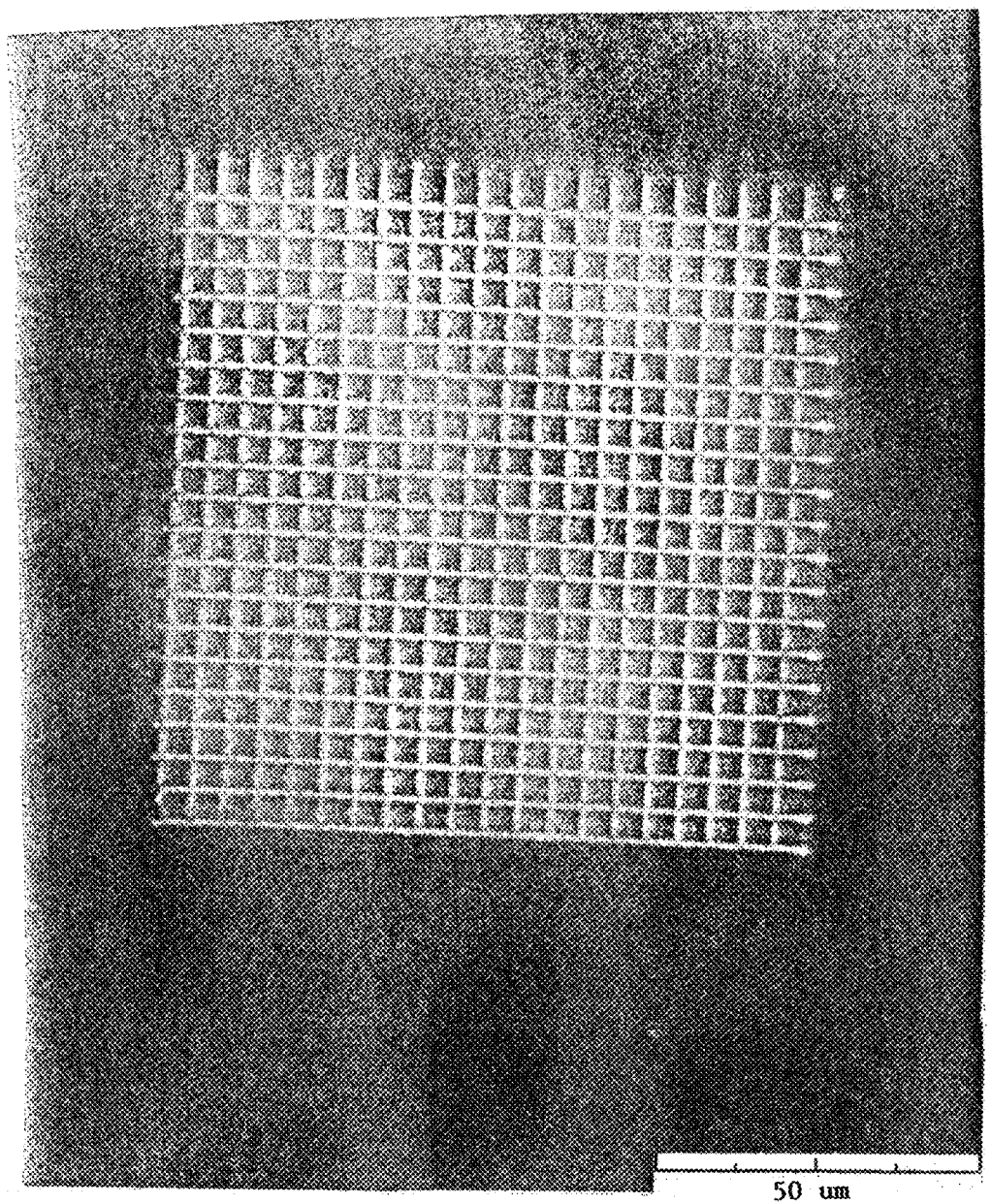
FIG. 2A is a microscope photograph of a line grating written above and orthogonal to another line grating in an optical, polymeric material produced by laser irradiation.
Figure 2B:
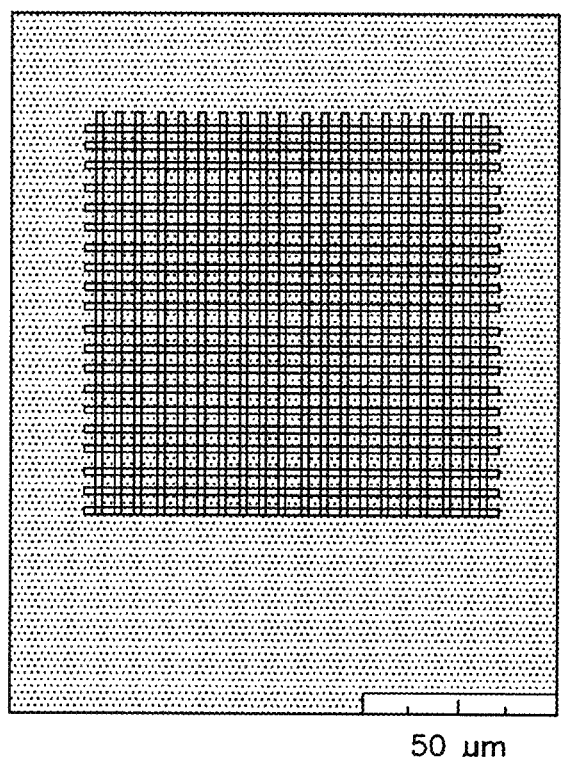
FIG. 2B is a schematic representation of the microscope photograph of FIG. 2B.

FIG. 2A is a microscopic photograph with contrasting background of one line grating written above and orthogonal to another line grating. FIG. 2B is a schematic representation of the microscope photograph of FIG. 2A. Each of the gratings has a similar dimensional structure to that described for FIG. 1 above. One line grating is positioned about 100 µm into the material, and the other line grating is positioned about 110 µm into the material for a center-line, grating separation of about 10 µm. Again, each of these line structures has a height (depth) of about 3 µm.

Figure 3A:
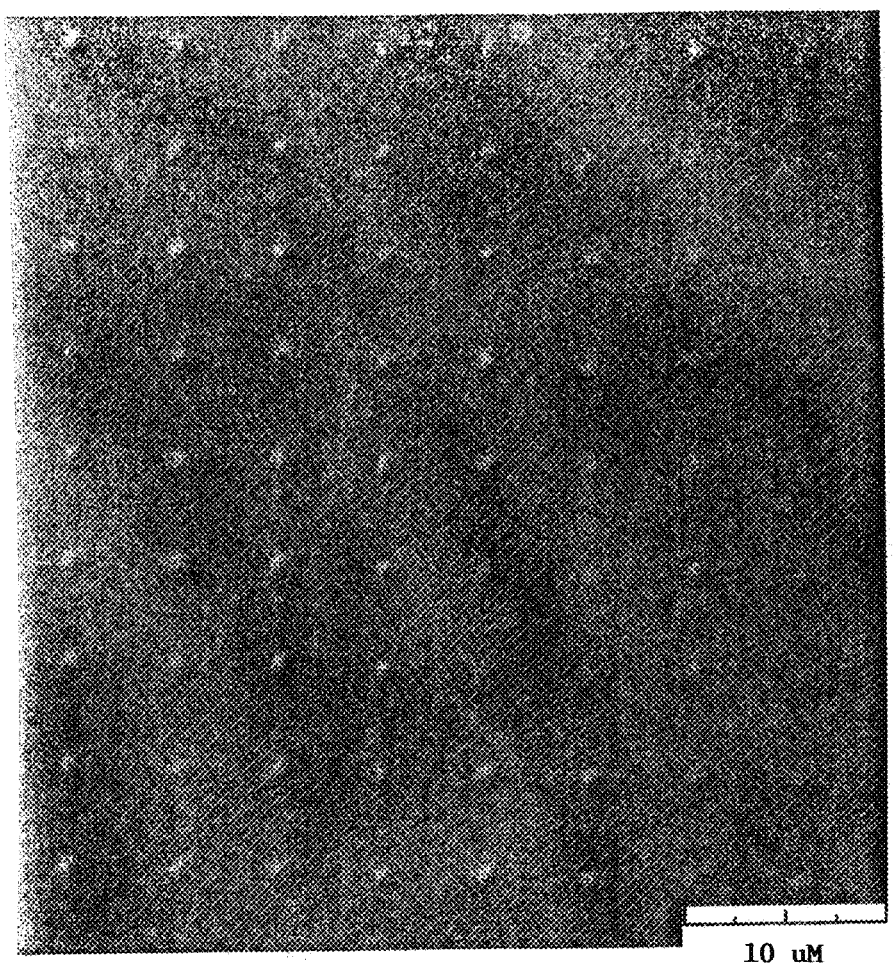
FIG. 3A is a microscope photograph of an array of cylinders etched in an optical, polymeric material produced by laser irradiation.
Figure 3B:
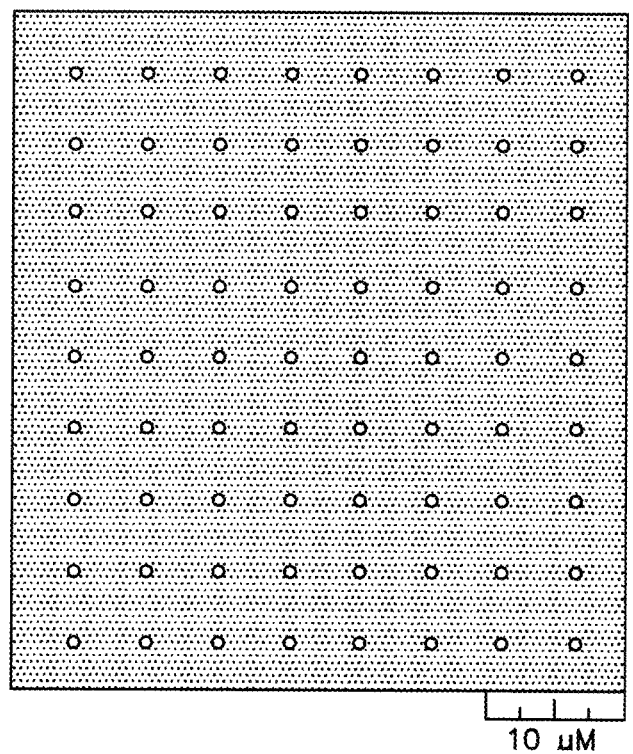
FIG. 3B is a schematic representation of the microscope photograph of FIG. 3A.

FIG. 3A is a microscopic photograph with contrasting background of an array of cylinders written into an optical material. FIG. 3B is a schematic representation of the microscope photograph of FIG. 3A. Each cylinder is about 1 µm in diameter with a height of about 3 µm. The cylinders are separated by about 5 µm. The cylinders were etched into the material at a distance of about 100 µm from the top surface of the material.

Figure 4A:
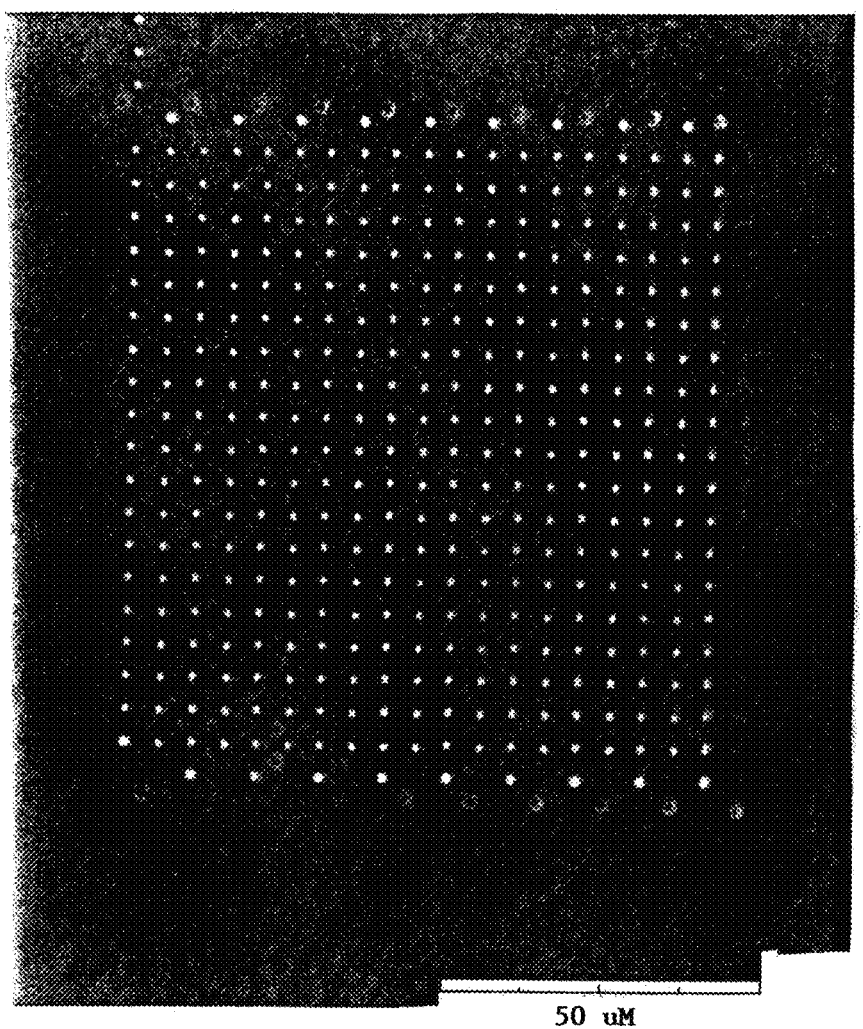
FIG. 4A is a microscope photograph of one array of cylinders (20×20) etched above and slightly offset to another array of cylinders (20×20) in an optical, polymeric material produced by laser irradiation.
Figure 4B:
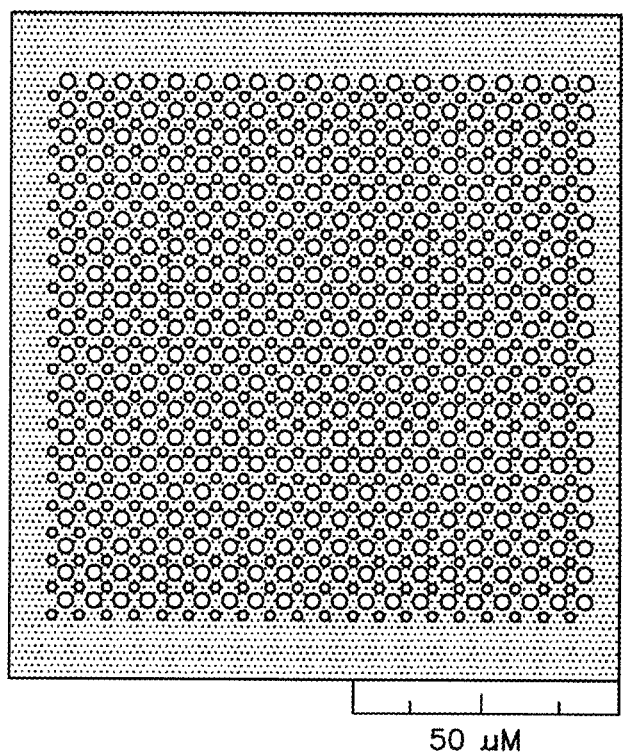
FIG. 4B is a schematic representation of the microscope photograph of FIG. 4A.

FIG. 4A is a microscopic photograph with contrasting background of one array of cylinders (20×20) written above and slightly offset to another array of cylinders (20×20). FIG. 4B is a schematic representation of the microscope photograph of FIG. 4A. Each of the cylinders has a similar dimensional structure to that described for FIG. 3 above. One array is positioned about 100 µm into the material, and the other array is positioned about 105 µm into the material for a center-line separation of about 5 µm. Each of the cylinders has a height (depth) of about 3 µm.

Figure 5:
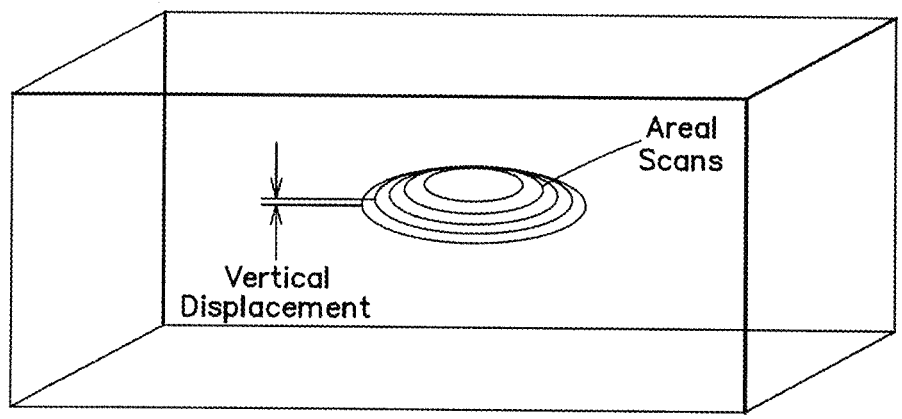
FIG. 5 is a schematic representation of a three-dimensional structure in an optical, polymeric material that can be produced by laser irradiation.
Figure 6:
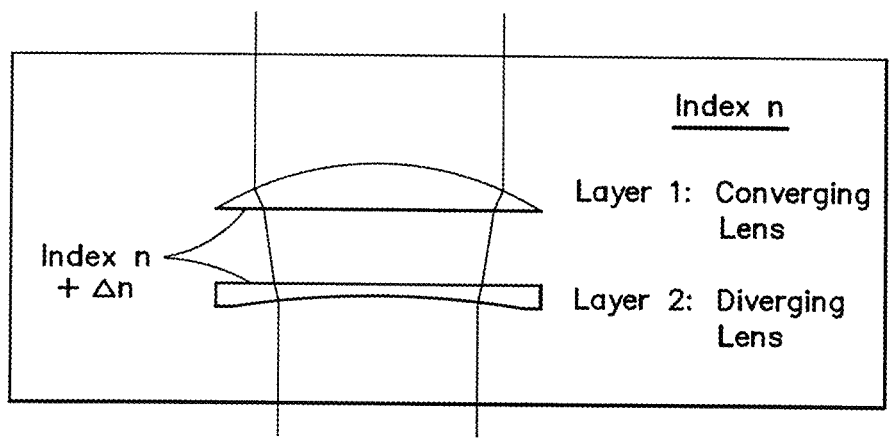
FIG. 6 is a schematic representation of creating a convex, plano or concave structure in an optical, polymeric material to yield a positive or negative correction.

The area-filled or volume-filled two- or three-dimensional structures can be formed by continuously scanning the laser over selected regions of the optical, polymeric material. Refractive-type optical devices can be micro-machined inside the volume of an optical, polymer material by repeatedly scanning a tightly focused beam of femtosecond pulses in an area segment. The area of the segment can be changed correspondingly with the depth of the scan, so as to produce three-dimensionally shaped lenses with spheric, aspheric, toroidal or cylindrical shapes as shown in FIG. 5. Although the refractive index change is positive (+0.02 to +0.06), these refractive corrective lenses can be made in various combinations of convex, plano- or concave to yield a positive correction, or negative correction, as shown in FIG. 6. The devices can be stacked vertically, written separately in different planes, so as to act as a single lens. Additional corrective layers can be written as desired.

As indicated by the micrographs of the refractive structures described the area-filled or volume-filled two- or three-dimensional structures one can create a pattern of grating lines, cylinders and radial patterns in optical materials, however, it is also possible to create other optical features using the irradiation method described herein. For examples, arrays of dots (e.g., having a dimension in the nanometer range) can be created by directing the laser beam at discrete points or spots within the material. Such an array can be arranged substantially on one plane or several such arrays can be created at different depths within the material. A material thus modified can be advantageously useful when light is not substantially scattered by the dots.

In one embodiment, the refractive structures are formed proximate to the top anterior surface of an intraocular lens. For example, a positive or negative lens element (three-dimensional) is formed within a 300 µm volume, or within a 100 µm volume, from the anterior surface of the lens. The term "anterior surface" is the surface of the lens that faces anterior chamber of a human eye.

A Laser and Optical Configuration for Modifying an Optical Material.

Figure 7:
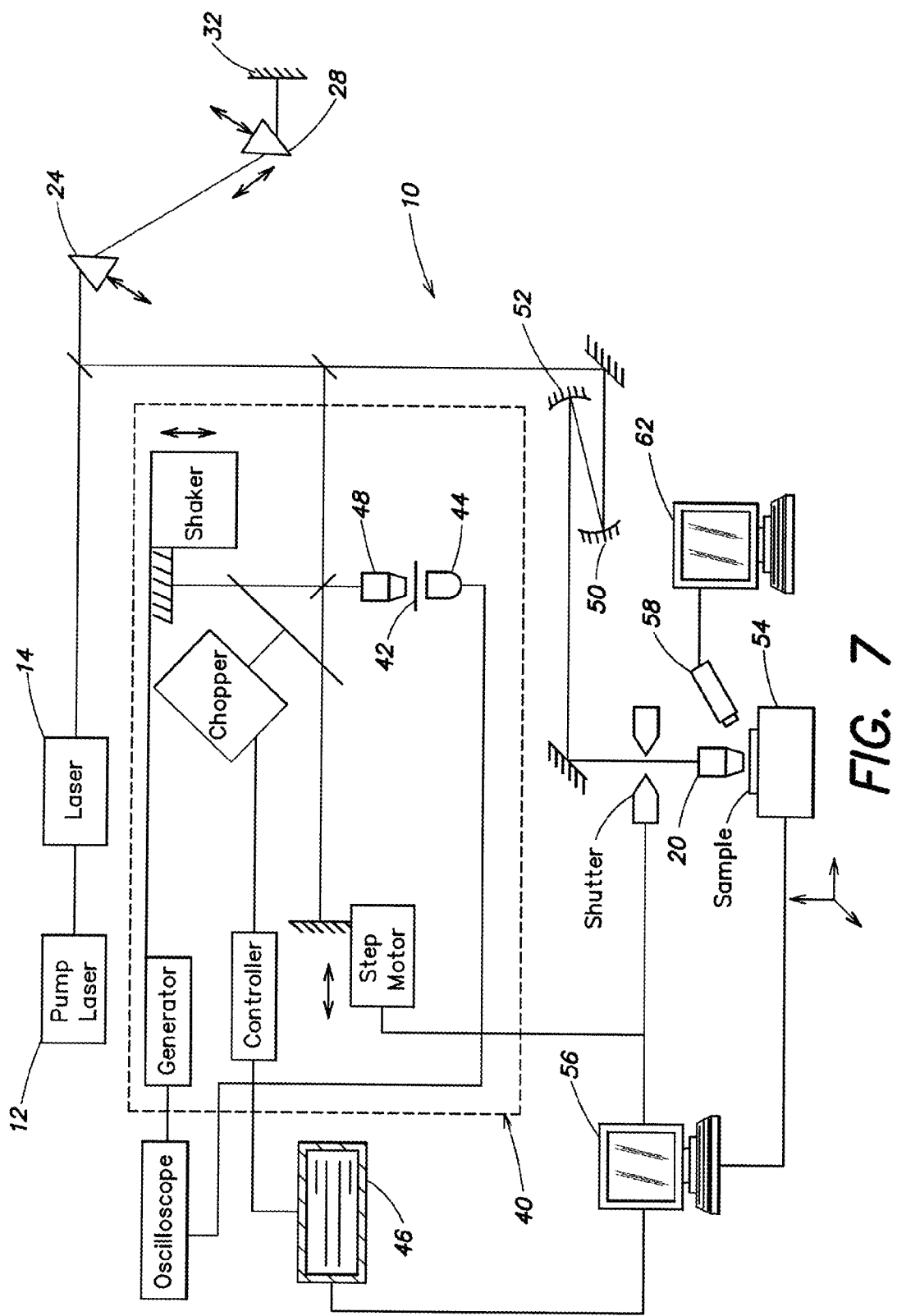
FIG. 7 is a schematic representation of the laser and optical system used to write the structures shown in FIGS. 1 to 4, 9, 10 and 12.

A non-limiting embodiment of a laser system 10 for irradiating an optical, polymeric material with a laser to modify the refractive index of the material in select regions is illustrated in FIG. 7. A laser source comprises a Kerr-lens mode-locked Ti:Sapphire laser 12 (Kapteyn-Murnane Labs, Boulder, Colo.) pumped by 4 W of a frequency-doubled Nd:YVO4 laser 14. The laser generates pulses of 300 mW average power, 30 fs pulse width and 93 MHz repetition rate at wavelength of 800 nm. Because there is a reflective power loss from the mirrors and prisms in the optical path, and in particular, from the power loss of the objective 20, the measured average laser power at the objective focus on the material is about 120 mW, which indicates the pulse energy for the femtosecond laser is about 1.3 nJ.

Due to the limited laser pulse energy at the objective focus, the pulse width must be preserved so that the pulse peak power is strong enough to exceed the nonlinear absorption threshold of the materials. Because a large amount of glass inside the focusing objective significantly increases the pulse width due to the positive dispersion inside of the glass, an extra-cavity, compensation scheme is used to provide the negative dispersion that compensates for the positive dispersion introduced by the focusing objective. Two SF10 prisms 24 and 28 and one ending mirror 32 form a two-pass one-prism-pair configuration. We used a 37.5 cm separation distance between the prisms to compensate the dispersion of the microscope objective and other optics within the optical path.

A collinear autocorrelator 40 using third-order harmonic generation is used to measure the pulse width at the objective focus. Both 2nd and 3rd harmonic generation have been used in autocorrelation measurements for low NA or high NA objectives. We selected third order surface harmonic generation (THG) autocorrelation to characterize the pulse width at the focus of the high-numerical-aperture objectives because of its simplicity, high signal to noise ratio and lack of material dispersion that second harmonic generation (SHG) crystals usually introduce. The THG signal is generated at the interface of air and an ordinary cover slip 42 (Corning No. 0211 Zinc Titania glass), and measured with a photomultiplier 44 and a lock-in amplifier 46. After using a set of different high-numerical-aperture objectives and carefully adjusting the separation distance between the two prisms and the amount of glass inserted, we selected a transform-limited 27-fs duration pulse, which is focused by a 60× 0.70NA Olympus LUCPlanFLN long-working-distance objective 48.

Because the laser beam will spatially diverge after it comes out of the laser cavity, a concave mirror pair 50 and 52 is added into the optical path in order to adjust the dimension of the laser beam so that the laser beam can optimally fills the objective aperture. A 3D 100 nm resolution DC servo motor stage 54 (Newport VP-25XA linear stage) and a 2D 0.7 nm resolution piezo nanopositioning stage (PI P-622.2CD piezo stage) are controlled and programmed by a computer 56 as a scanning platform to support and locate the samples. The servo stages have a DC servo-motor so they can move smoothly between adjacent steps. An optical shutter controlled by the computer with 1 ms time resolution is installed in the system to precisely control the laser exposure time. With customized computer programs, the optical shutter could be operated with the scanning stages to micro-machine different patterns in the materials with different scanning speed at different position and depth and different laser exposure time. In addition, a CCD camera 58 along with a monitor 62 is used beside the objective 20 to monitor the process in real time.

The method and optical apparatus described above can be used to modify the refractive index of an intraocular lens following the surgical implantation of the intraocular lens in a human eye.

Accordingly, the invention is directed to a method comprising identifying and measuring the aberrations resulting from the surgical procedure. Once the aberrations are identified and quantified using methods well known in the art of ophthalmology, this information is processed by a computer. Of course, information related to the requisite vision correction for each patient can also be identified and determined, and this information can also be processed by a computer. There are a number of commercially available diagnostic systems that are used to measure the aberrations. For example, common wavefront sensors used today are based on the Schemer disk, the Shack Hartmann wavefront sensor, the Hartmann screen, and the Fizeau and Twymann-Green interferometers. The Shack-Hartmann wavefront measurement system is known in the art and is described in-part by U.S. Pat. Nos. 5,849,006; 6,261,220; 6,271,914 and 6,270,221. Such systems operate by illuminating a retina of the eye and measuring the reflected wavefront.

Once the aberrations are identified and quantified, the computer programs determine the position and shape of the optical structures to be written into the lens material to correct for those aberrations or to provide vision correction to the patient. These computer programs are well known to those of ordinary skill in the art. The computer than communicates with the laser-optical system and select regions of the lens are irradiated with a laser having a pulse energy from 0.05 nJ to 1000 nJ.

The Optical, Hydrogel Polymeric Materials

The optical, hydrogel polymeric materials that can be irradiated with a laser according to the methods described in this application can be any optical, hydrogel polymeric material known to those of ordinary skill in the polymeric lens art, particularly those in the art familiar with optical polymeric materials used to make intraocular lenses. Non-limiting examples of such materials include those used in the manufacture of ophthalmic devices, such as siloxy-containing polymers, acrylic, hydrophilic or hydrophobic polymers or copolymers thereof. The forming of the refractive structures is particularly suited for modifying the refractive index in select and distinct regions of a polymeric, optical silicone hydrogel, or a polymeric, optical non-silicone hydrogel.

The term "hydrogel" refers to an optical, polymeric material that can absorb greater than 10% by weight water based on the total hydrated weight. In fact, many of the optical, hydrogel polymeric materials will have a water content greater than 15% or greater than 20%. For example, many of the optical, hydrogel polymeric materials will have a water content from 15% to 60% or from 15% to 40%.

The optical, hydrogel polymeric materials are of sufficient optical clarity, and will have a relatively high refractive index of approximately 1.40 or greater, preferably 1.48 or greater. Many of these materials are also characterized by a relatively high elongation of approximately 80 percent or greater.

In one embodiment, the optical polymeric materials are prepared as a copolymer from at least three monomeric components. The first monomeric component is present in the copolymer in an amount of at least 60% by weight, and its homopolymer will have a refractive index of at least 1.50, preferably at least 1.52 or at least 1.54. The second monomeric component is present in the copolymer in an amount from 3% to 20% or from 3% to 10%, by weight. The first and second monomeric components together represent at least 70% by weight of the copolymer. The term "homopolymer" refers to a polymer that is derived substantially completely from the respective monomeric component. Minor amounts of catalysts, initiators and the like can be included, as is conventionally the case, in order to facilitate the formation of the homopolymer.

Particularly useful first monomeric components include styrene, vinyl carbazole, vinyl naphthalene, benzyl(meth)acrylate, phenyl(meth)acrylate, naphthyl(meth)acrylate, 2-phenoxyethyl(meth)acrylate, 2,3-dibromopropyl-(meth)acrylate and any one mixture thereof. Particularly useful second monomeric components include n-butyl(meth)acrylate, n-hexyl(meth)acrylate, 2-ethylhexyl-(meth)acrylate, 2-ethoxyethyl(meth)acrylate, 2,3-dibromopropyl(meth)acrylate, 1,1-dihydroperfluorobutyl(meth)acrylate and any one mixture thereof.

The third monomeric component corresponds to the compounds of general formula I through general formula IV.

The copolymer can further include a fourth monomeric component derived from a hydrophilic monomeric component. The hydrophilic component is present in an amount, from 2% to 30% by weight of the copolymer. The hydrophilic component is preferably present in an amount of less than about 20% by weight of the copolymer. Copolymers which include about 10% by weight or more of a hydrophilic monomeric component tend to form hydrogels if placed in an aqueous environment. The term "hydrophilic monomeric component" refers to compounds which produce hydrogel-forming homopolymers, that is homopolymers which become associated with at least 25% of water, based on the weight of the homopolymer, if placed in contact with an aqueous solution.

Specific examples of useful hydrophilic monomeric components include N-vinyl pyrrolidone; hydroxyalkyl(meth)acrylates such as 2-hydroxyethyl(meth)acrylate, 3-hydroxypropyl(meth)acrylate, 3-hydroxypropyl(meth)acrylate, 4-hydroxybutyl(meth)acrylate, 2,3-dihydroxypropyl(meth)acrylate and the like; acrylamide; N-alkyl acrylamides such as N-methyl acrylamide, N-ethyl acrylamide, N-propyl acrylamide, N-butyl acrylamide and the like; acrylic acid; methacrylic acid; and the like and any one mixture thereof.

The polymeric optical materials will likely include a crosslinking component that can form crosslinks with at least the first or the second monomeric components. Preferably, the crosslinking component is multi-functional and can chemically react with both the first and second monomeric components. The crosslinking component is often present in a minor amount relative to the amounts of the first and second monomeric components. Preferably, the crosslink component is present in the copolymer in an amount of less than about 1% by weight of the copolymer. Examples of useful crosslinking components include ethylene glycol dimethacrylate, propylene glycol dimethacrylate, ethylene glycol diacrylate and the like and mixtures thereof.

In one embodiment, the optical polymeric materials can be prepared from one or more aromatic (meth)acrylate monomers having the formula:

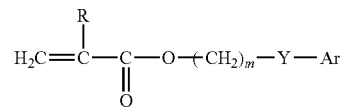

wherein: R is H or $CH_3$; m is an integer selected from 0 to 10; Y is nothing, O, S, or NR wherein R is H, $CH_3$, $C_2$-$C_6$alkyl, iso-$OC_3H_7$, phenyl or benzyl;

Ar is any aromatic ring, e.g., phenyl, which can be unsubstituted or substituted with H, $CH_3$, $C_2H_5$, n-$C_3H_7$, iso-$C_3H_7$, $OCH_3$, $C_6H_{11}$, Cl, Br, phenyl or benzyl; and a crosslinking component.

Exemplary aromatic (meth)acrylate monomers include, but are not limited to:
2-ethylphenoxy(meth)acrylate, 2-ethylthiophenyl(meth)acrylate, 2-ethylaminophenyl(meth)acrylate, phenyl-(meth)acrylate, benzyl(meth)acrylate, 2-phenylethyl(meth)acrylate, 3-phenylpropyl-(meth)acrylate, 4-phenylbutyl(meth)acrylate,
4-methylphenyl(meth)acrylate, 4-methylbenzyl(meth)acrylate, 2-2-methylphenylethyl(meth)acrylate, 2-3-methylphenylethyl(meth)acrylate, 2-4-methylphenylethyl(meth)acrylate, 2-(4-propylphenyl)ethyl(meth)acrylate, 2-(4-(1-methylethyl)phenyl)ethyl methacrylate, 2-(4-methoxyphenyl)ethyl methacrylate and the like.

Generally, if the optical, polymeric material is prepared with both an aromatic acrylate and an aromatic methacrylate as defined by the formula above, the materials will generally comprise a greater mole percent of aryl acrylate ester residues than of aryl methacrylate ester residues. It is preferred that the aryl acrylate monomers constitute from about 60 mole percent to about 90 mole percent of the polymer, while the aryl methacrylate monomers constitute from about 5 mole percent to about 40 mole percent of the polymer. Most preferred is a polymer comprising about 60-70 mole percent 2-phenylethyl acrylate and about 30-40 mole percent 2-phenylethyl methacrylate.

In another embodiment, the optical, polymeric materials will have a fully hydrated (equilibrium) water content from 5% to 15% by weight, which also helps to minimize the degree of hazing following thermal stress as described as well as minimize the formation of water vacuoles in vivo. To achieve the desired water content applicants have discovered that one could include a hydrophilic, aromatic monomer having a formula, G-D-Ar, wherein Ar is a C6-C14 aromatic group having a hydrophilic substituent, in the polymerizable compositions. D is a divalent linking group, and G is a polymerizable ethylenic site, One particular hydrophilic aromatic monomer is represented by formula

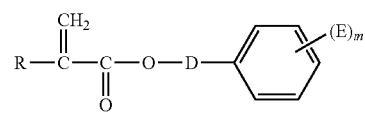

wherein R is hydrogen or $CH_3$; D is a divalent group selected from the group consisting of straight or branched $C_1$-$C_{10}$ hydrocarbons, and E is selected from the group consisting of carboxy, carboxamide, and monohydric and polyhydric alcohol substituents. Exemplary hydrophilic substituents include, but are not limited to, —COOH, —$CH_2$—$CH_2OH$, —(CHOH)$_2$CH$_2$OH, —CH$_2$—CHOH—CH$_2$OH, poly(alkylene glycol), —C(O)O—NH$_2$ and —C(O)—N(CH$_3$)$_2$.

Exemplary hydrophilic, aromatic monomers are represented by the following

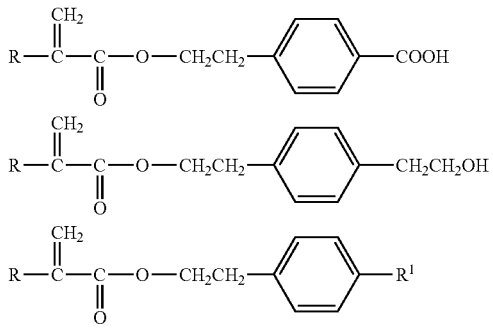

wherein R is hydrogen or CH$_3$ and R$^1$ is —C(O)O—NH$_2$ or —C(O)—N(CH$_3$)$_2$.

In another embodiment, the optical, polymeric material is prepared from a first aryl monomeric component, which is present in 5-25% by weight, the second monomeric component is 2-hydroxyethyl(meth)acrylate, which is present from 30 to 70% by weight; and 5 to 45% by weight of a another alkyl(meth)acrylate selected from the group consisting of methyl(meth)acrylate, ethyl(meth)acrylate, propyl(meth)acrylate, butyl(meth)acrylate, pentyl(meth)acrylate, hexyl meth)acrylate, heptyl(meth)acrylate, nonyl(meth)acrylate, stearyl meth)acrylate, octyl(meth)acrylate, decyl(meth)acrylate, lauryl(meth)acrylate, pentadecyl(meth)acrylate and 2-ethylhexyl(meth)acrylate. Among the alkyl(meth)acrylates those containing 1 to 3 carbon atoms of alkyl group are preferred.

Exemplary aryl monomeric components include ethylene glycol phenyl ether acrylate (EGPEA), poly(ethylene glycol phenyl ether acrylate) (polyEGPEA), phenyl methacrylate, 2-ethylphenoxy methacrylate, 2-ethylphenoxy acrylate, hexylphenoxy methacrylate, hexylphenoxy acrylate, benzyl methacrylate, 2-phenylethyl methacrylate, 4-methylphenyl methacrylate, 4-methylbenzyl methacrylate, 2-2-methyphenylethyl methacrylate, 2-3-methylphenylethyl methacrylate, 2-4-methylphenylethyl methacrylate, 2-(4-propylphenyl) ethyl methacrylate, 2-(4-(1-methylethyl)pheny)ethyl methacrylate, 2-(4-methoxyphenyl)ethylmethacrylate, 2-(4-cyclohexylpheny)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates, and including mixtures thereof. EGPEA and polyEGPEA are two of the more preferred first monomeric components.

In another embodiment, the optical, polymeric material is prepared from a hydrophilic acrylic that comprises about 90% (by weight) N-vinylpyrrolidone (NVP) and about 10% (by weight) 4-t-butyl-2-hydroxycyclohexyl methacrylate. This methacrylate hydrogel can absorb about 80% (by weight) water because of the high percentage of NVP. Its refractive index when hydrated is very close to the index of water. Another hydrophilic acrylic of interest is referred to as HEMA B, which is a poly(2-hydroxyethyl methacrylate) cross-linked with about 0.9% (by weight) of ethylene glycol dimethacrylate ("EGDMA"). This HEMA-hydrogel can absorb about 37% (by weight) water.

One particular hydrophilic, acrylic material of interest is based upon a commercially available IOL sold in the market by Bausch & Lomb under the tradename Akreos®. This acrylic material comprises about 80% by weight HEMA and 20 wt % MMA.

The optical, polymeric material can also be prepared by copolymerizing a specific monomer mixture comprising perfluorooctylethyloxypropylene(meth)acrylate, 2-phenylethyl (meth)acrylate, an alkyl(meth)acrylate monomer having the following general formula,

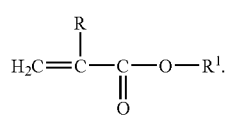

wherein R is hydrogen or methyl and R$^1$ is a linear or branched C$_4$-C$_{12}$ alkyl group, and a crosslinking monomer. An examplary list of alkyl(meth)acrylate monomer include n-butyl acrylate, isobutyl acrylate, isoamyl acrylate, hexyl acrylate, 2-ethylhexyl acrylate, octyl acrylate, isooctyl acrylate, decyl acrylate, isodecyl acrylate, and the like.

The perfluorooctylethyloxypropylene(meth)acrylate is present from 5% to 20% by weight, the 2-phenylethyl(meth) acrylate is present from 40% to 60% by weight, the alkyl (meth)acrylate monomer is present from 30% to 50% by weight and the crosslinking agent is present from 0.5% to 4% by weight.

The optical, polymeric component will likely include a crosslinking agent. The copolymerizable crosslinking agent(s) useful in forming the copolymeric material of the invention include any terminally ethylenically unsaturated compound having more than one unsaturated group. Preferably, the crosslinking agent includes a diacrylate or a dimethacrylate. The crosslinking agent may also include compounds having at least two (meth)acrylate and/or vinyl groups. Particularly preferred crosslinking agents include diacrylate compounds The optical, polymeric materials are prepared by generally conventional polymerization methods from the respective monomeric components. A polymerization mixture of the monomers in the selected amounts is prepared and a conventional thermal free-radical initiator is added. The mixture is introduced into a mold of suitable shape to form the optical material and the polymerization initiated by gentle heating. Typical thermal, free radical initiators include peroxides, such as benzophenone peroxide, peroxycarbonates, such as bis-(4-t-butulcyclohexyl)peroxydicarbonate, azonitriles, such as azobisisobytyronitrile, and the like. A preferred initiator is bis-(4-t-butylcyclohexyl)peroxydicarbonate (PERK). Alternatively, the monomers can be photopolymerized by using a mold which is transparent to actinic radiation of a wavelength capable of initiating polymerization of these acrylic monomers by itself. Conventional photoinitiator compounds, e.g., a benzophenone-type photoinitiator, can also be introduced to facilitate the polymerization.

While specific embodiments of the present invention have been described in the foregoing, it will be appreciated by those skilled in the art that many equivalents, modifications, substitutions, and variations may be made thereto without departing from the spirit and scope of the invention as defined in the claims.

EXAMPLES

Example 1

Preparation of Akreos® IOL with 17% Coumarin-1

Coumarin 1 dye (2.5 g) is dissolved in an ethanol-water mixture containing 10 mL ethanol and 5 mL water. Dry weight of the Akreos sample is recorded. The samples are hydrated in pure water and the mass is recorded. Following the hydration step, the samples are soaked in the ethanol-water mixture containing the coumarin 1 dye until a constant mass is attained. The mass after soaking in the dye solution is recorded. Mass of the dye doped is calculated as the difference between the mass after soaking in the solution, and the dry mass multiplied by the mass concentration of the dye in the ethanol-water solution. Percentage of the dye doped is calculated as the ratio of mass of coumarin 1 dye doped over the dry mass multiplied by 100.

Example 2

Forming Structures in Akreos® IOL Materials

The optical system described was used to form line structures in select regions of optical materials. Experiments were conducted with Akreos® IOL materials with and without photosensitizer. Akreos® IOL materials comprise about 80 wt % HEMA and 20 wt % MMA with a water content of about 26% using similar process conditions described above.

The hydrated sample was mounted horizontally on the scanning platform, and the femtosecond laser beam was directed vertically downward through the high-numerical-aperture objective and was focused inside the bulk material, as shown in FIG. 7, at a depth of about 100 µm from the upper surface of the sample. Periodic gratings structures were created with a scanning speed of 0.4 µm/sec in an X-Y plane perpendicular to the laser beam. An Olympus BX51 Model microscope was used to observe the gratings that were created inside these three materials.

The microscope images showed periodically parallel gratings inside the samples with 5-µm spacing. The gratings were difficult to see in bright-field microscope, indicating that these gratings exhibit low scattering. The width of the gratings was about 1 µm, which was significantly smaller than the laser focus diameter of 2.5 µm that was measured using a knife-edge method. Therefore, the modified region is still within the laser irradiation focus volume although there would be heat accumulation generated in the process.

A cross section of the irradiated materials revealed that the cross section of the gratings was elliptical with the longer axis oriented in the direction of the laser beam, indicating that there was a larger laser intensity distribution in this direction. By carefully adjusting the cover-slip correction of the objective, this spherical aberration could be minimized.

Figure 8A:
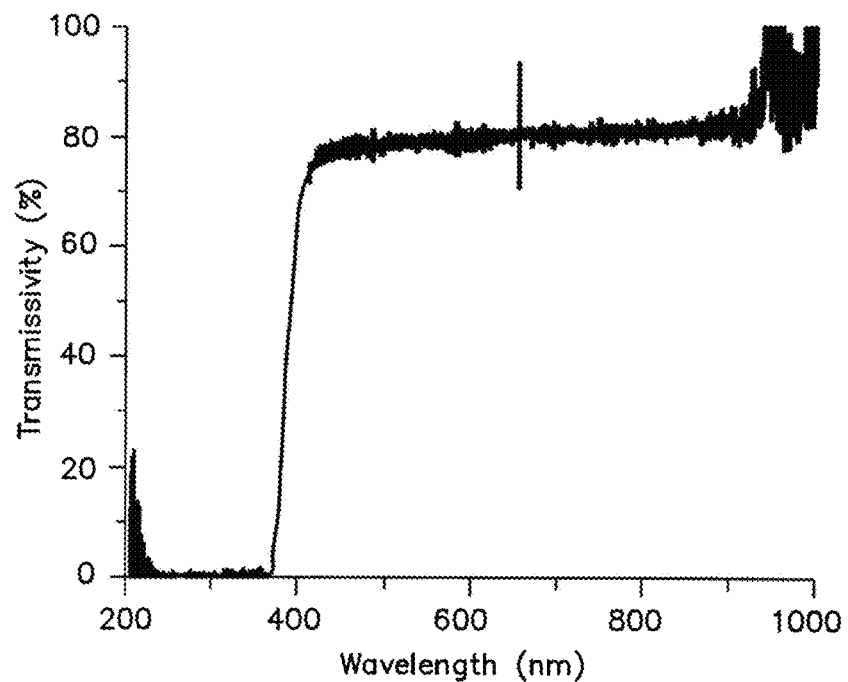
FIG. 8A is a transmission spectrum of a hydrated Akreos® IOL without photosensitizer.
Figure 8B:
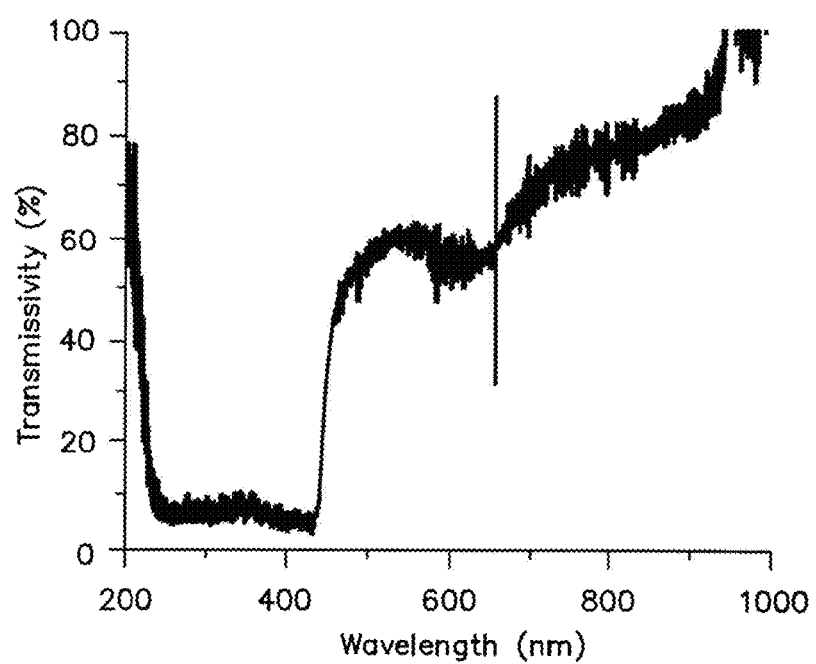
FIG. 8B is a transmission spectrum of a hydrated Akreos® IOL doped with a solution containing 17 wt. % coumarin-1.
Figure 9A:
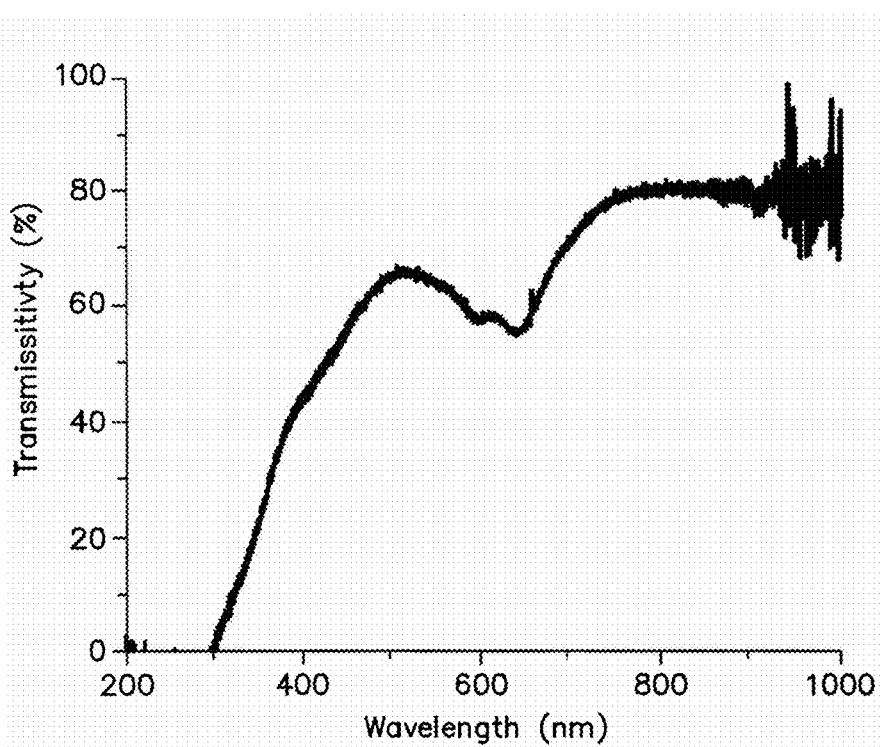
FIG. 9A is a transmission spectrum of a hydrated Pure Vision® silicone hydrogel without photosensitizer.
Figure 9B:
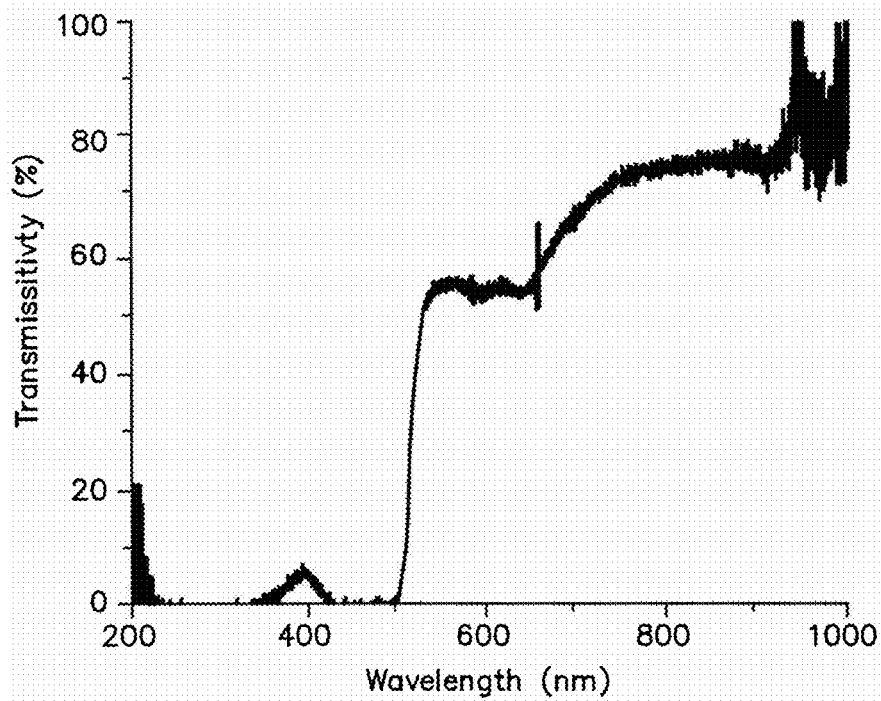
FIG. 9B is a transmission spectrum of a hydrated Pure Vision® silicone hydrogel doped with 0.17 wt. % fluorescein.
Figure 10:
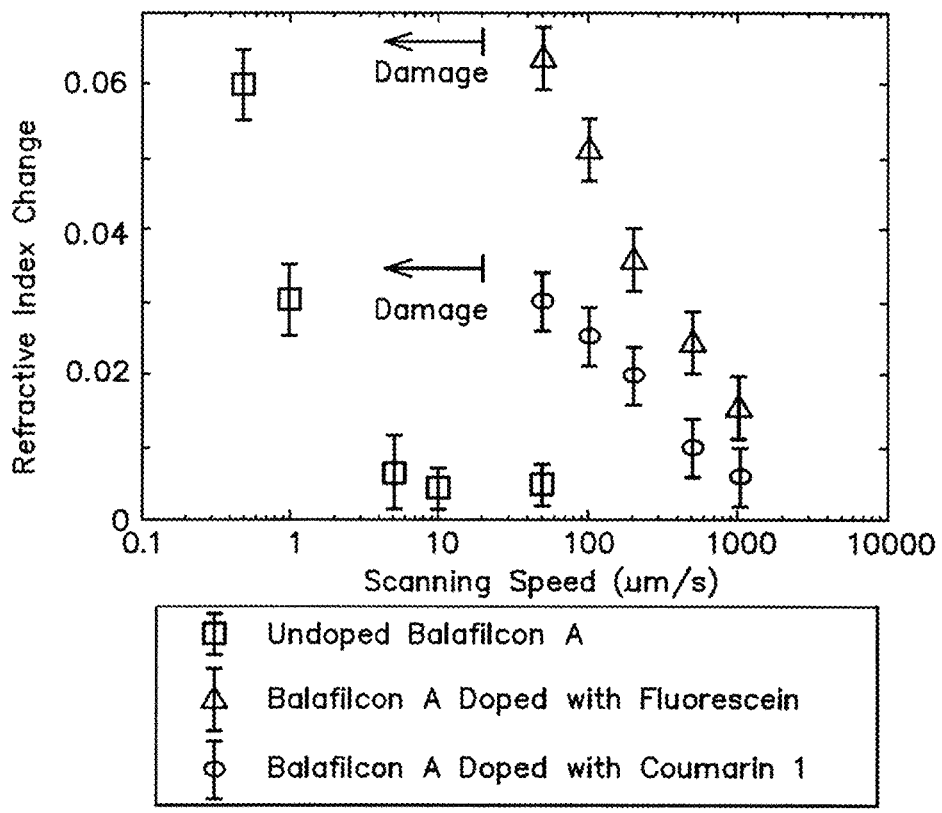
FIG. 10 is a plot of change in refractive index vs. scan rate in balafilcon A films (undoped and doped with fluorescein and coumarin-1.

As indicated in FIGS. 8A and 8B, the incorporation of coumarin-1 into an Akreos® IOL provided a red shift in the transmission spectrum of an Akreos® IOL material of about 50 nm. The Akreos® IOL material with coumarin-1 has a relatively significant absorption profile at 400 nm and to about 425 nm, whereas an Akreos® IOL material without photosensitizer is essentially transparent at these wavelengths.

Refractive structures micromachined within Akreos® IOL materials at a depth of about 200 µm from the top irradiated surface were formed. The irradiation process was conducted at 160 mW average power and a scan rate of 50 µm/s. The refractive structures micromachined in the Akreos® IOL material without photosensitizer provide little, if any, change in refractive index, $\Delta RI \ll 0.005$ (visible detection limit of the structures). In fact, it is very difficult to see the refractive structures in the material even with phase contrast enhancement. In contrast, the refractive structures micromachined in the Akreos® IOL material with 17% coumarin-1 at the identical power and scan rate provide a very significant change in refractive index, $\Delta RI > 0.06$. The refractive structures are clearly visible with phase contrast enhancement.

The change in the refractive power of the micromachined structures (the magnitude of change in refractive index) can be varied based on the scan rate and laser power. More importantly, one can form refractive structures in Akreos® IOL materials with 17% coumarin-1 at a scan rate of 1 mm/s, and with a $\Delta RI$ of about 0.02 to 0.3. A very surprising and exciting result since one would have to scan at about 10 µm/s to generate a similar refractive structure in an Akreos® IOL material without photosensitizer. The presence of the coumarin-1 allows one to increase the scan rate nearly 100-fold. Moreover, even with a relatively low laser power, i.e., 60 mW, one can still generate refractive structures with a $\Delta RI$ of about 0.005.

Example 3

Preparation of Pure Vision® Silicone Hydrogel with 0.07 wt. % Fluorescein

Fluorescein (0.25 g) dye is dissolved in an ethanol-water mixture containing 50 mL ethanol and 50 mL water. Dry weight of the Pure Vision sample is recorded. The samples are hydrated in pure water and the mass is recorded. Following the hydration step, the samples are soaked in the ethanol-water mixture containing fluorescein dye until a constant mass is attained. The mass after soaking in the dye solution is recorded. Mass of the dye doped is calculated as the difference between the mass after soaking in the solution, and the dry mass multiplied by the mass concentration of the dye in the ethanol-water solution. Percentage of the dye doped is calculated as the ratio of mass of Fluorescein dye doped over the dry mass multiplied by 100.

Example 4

Forming Structures in Balafilcon A Silicone Hydrogel

The optical system as described in Example 2 was used to form line structures in select regions of hydrated balafilcon A (Pure Vision®) silicone hydrogel materials. Experiments were conducted with and without the photosensitizer, fluorescein.

Figure 11:
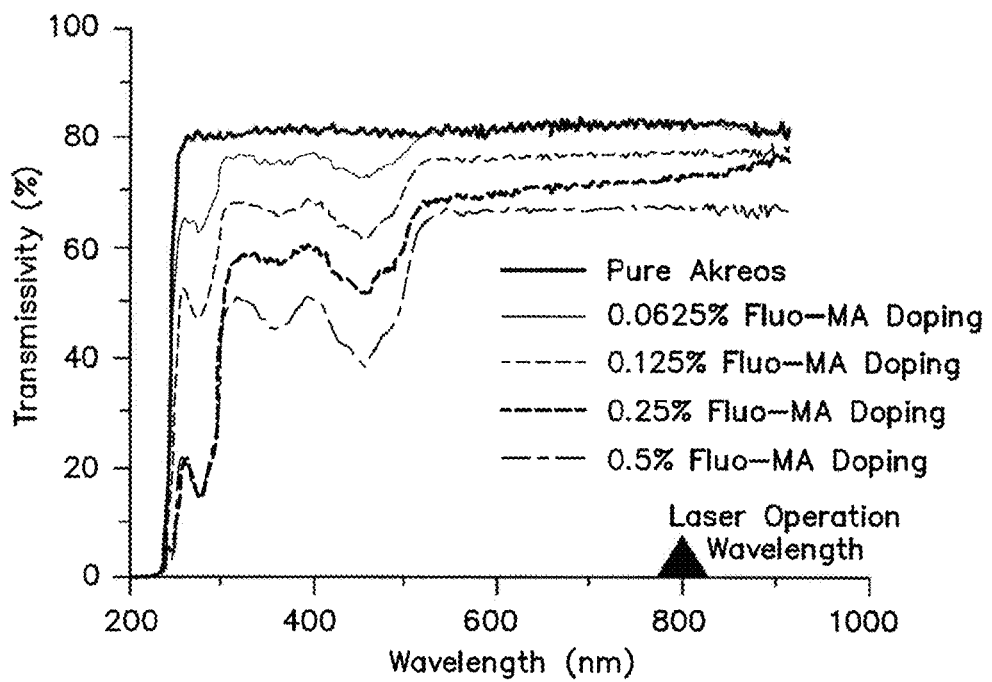
FIG. 11 are the transmission spectra of the hydrogel materials of Example 5.
Figure 12:
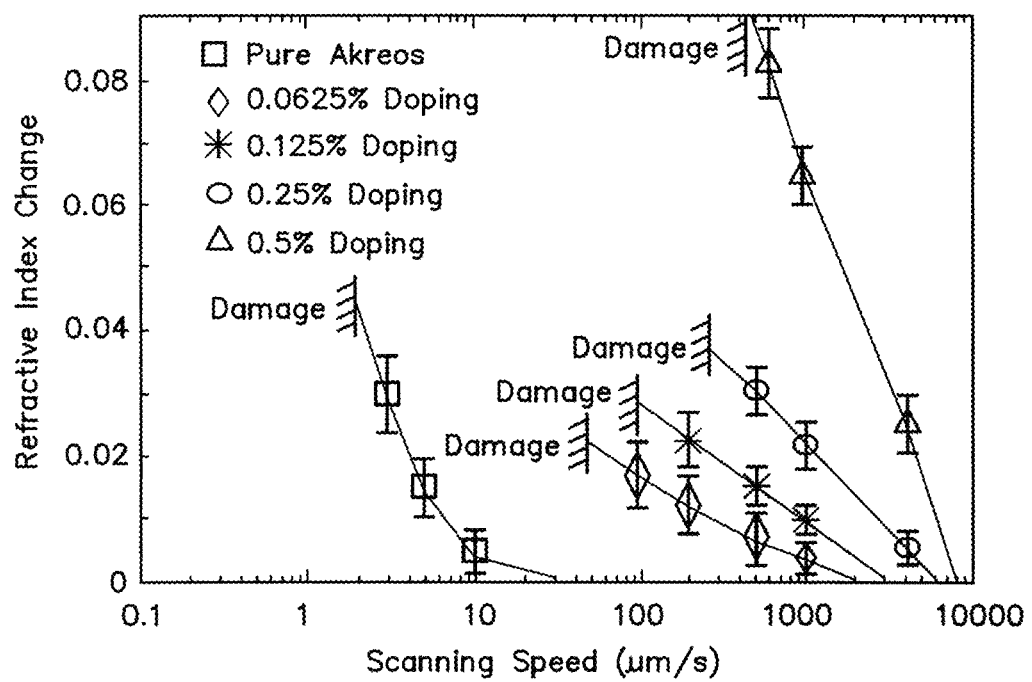
FIG. 12 is a plot of the measured change in refractive index at different scan rates for the hydrogel materials of Example 5.
Figure 13A:
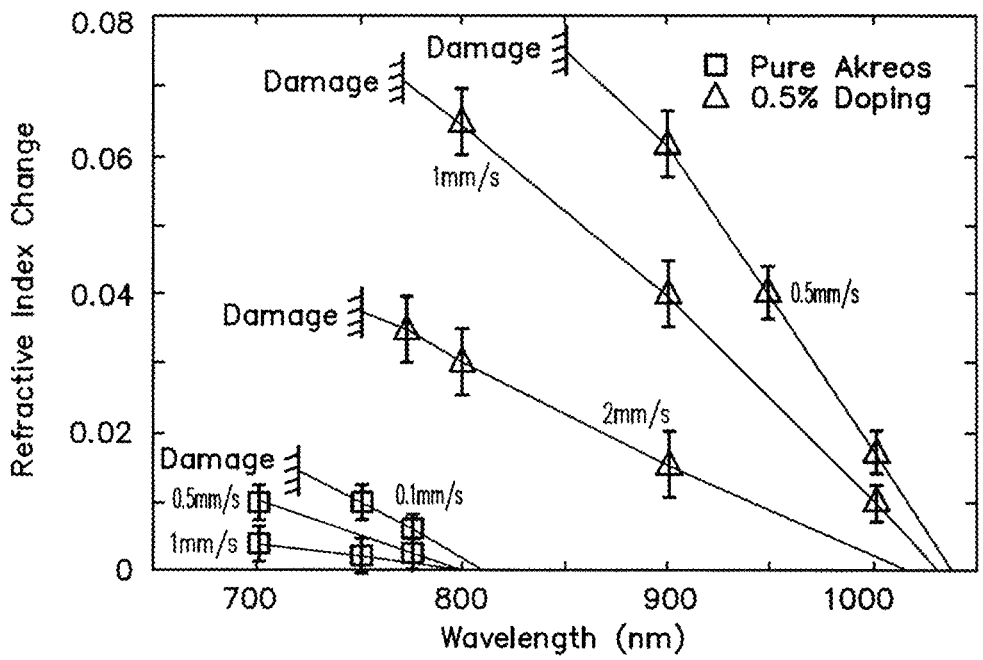
FIGS. 13A and 13B are plots of the measured change in refractive index at various wavelengths at average pulse energies of 1.5 nJ and 2 nJ, respectively, for the hydrogel materials of Examples 5A and 5E.
Figure 13B:
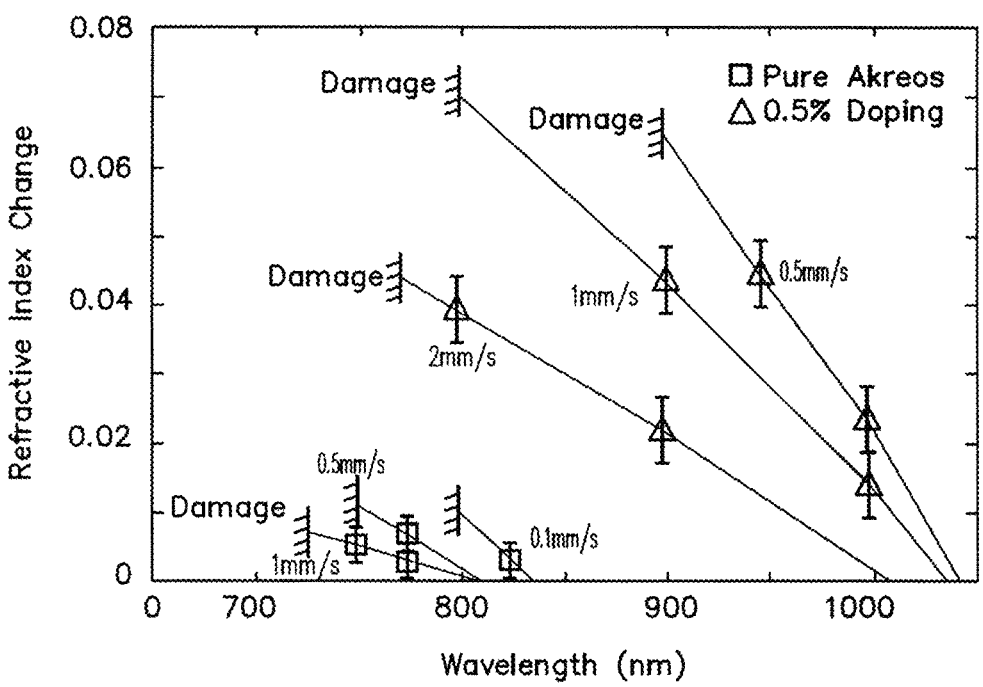

As indicated in FIGS. 11A and 11B, the incorporation of fluorescein into a balafilcon A silicone hydrogel provided a red shift in the transmission spectrum of at least 150 nm. The balafilcon A silicone hydrogel with fluorescein has a relatively significant absorption profile at 500 nm, FIG. 12B whereas a silicone hydrogel without photosensitizer is essentially transparent at these wavelengths, FIG. 12A.

Refractive structures were micromachined in a balafilcon A silicone hydrogel at a depth of about 200 µm from the top irradiated surface. The irradiation process was conducted at 60 mW, and a scan rate of 0.5 µm/s. The refractive structures micromachined in the balafilcon A silicone hydrogel without photosensitizer provide little, if any, change in refractive index, $\Delta RI \ll 0.005$ (visible detection limit of the structures).

In fact, it is very difficult to see the refractive structures in the material even with phase contrast enhancement. In contrast, the refractive structures micromachined in the balafilcon A silicone hydrogel with 0.17 wt. % fluorescein at the identical power and at a scan rate of 5.0 μm/s (a ten-fold increase over the undoped balafilcon A) provide a very significant change in refractive index, ΔRI of about 0.02 to 0.03. The refractive structures are clearly visible with phase contrast enhancement. Moreover, even with a relatively low laser power, i.e., 60 mW, one can still generate refractive structures with a ΔRI of about 0.01 with a scan rate of 1 mm/s.

A plot showing the change in refractive index vs. scan rate in balafilcon A materials; undoped or doped with fluorescein or coumarin-1. The plot demonstrates the significant enhancement of the photo-adjusting affect in the hydrogel material doped with a photosensitizer. The doping of the material permits one to increase the scan rate of the laser through the material, i.e., form refractive structures in the material, by nearly 100-fold to achieve a comparable modification of the refractive index in the material.

In Examples 2 and 4, the refractive structures (line gratings) were investigated by focusing an unpolarized He—Ne laser beam with a wavelength of 632.8 nm on these gratings and monitoring the diffraction pattern. The diffraction angles showed good agreement with the diffraction equation $$m\lambda = d \sin \theta \quad (1)$$

where m is the diffraction order, λ is the wavelength of the incident laser beam which here is 632.8 nm, and d is the grating period.

The diffraction efficiency of the grating can be measured, and since the efficiency is a function of the refractive index change, it may be used to calculate the refractive index change in the laser irradiation region. Consider the grating as a phase grating, its transmittance function could be written as $$t(x_0, y_0) = (e^{i\phi_2} - e^{i\phi_1}) rect\left(\frac{x_0}{a}\right) * \frac{1}{d} comb\left(\frac{x_0}{d}\right) + e^{i\phi_1} \quad (2)$$

where a is the grating line width, d is the groove spacing, $\phi_2$ and $\phi_1$ are the phase delays through the lines and ambient region respectively, $\phi_2 = 2\pi \times (n+\Delta n) \times b/\lambda$ and $\phi_1 = 2\pi \times n \times b/\lambda$, b is the thickness of the grating line, n is the average refractive index of the material, Δn is the average refractive index change in the grating lines, and λ is the incident light wavelength of the measurement (632.8 nm). Here, the grating line width is 1 μm and the thickness is 3 μm. The index change within the laser effect region can be approximated to be uniform. The convolution theorem can be used to calculate the spectrum of the grating such as $$T(f_x, f_y) = F\{t(x_0,y_0)\} = (e^{i\phi_2} - e^{i\phi_1})a \sin c(af_x) comb(df_x) \delta(f_y) + e^{i\phi_1} \delta(f_x, f_y) \quad (3)$$

Then, the intensity distribution of the grating diffraction pattern is:

$$I(x, y) = \left(\frac{1}{\lambda z}\right)^2 \times \left[(e^{i\phi_2} - e^{i\phi_1})\frac{a}{d}\sum_{n=-\infty}^{\infty} sinc\left(\frac{an}{d}\right)\delta\left(\frac{x}{\lambda z} - \frac{n}{d}, \frac{y}{\lambda z}\right) + e^{i\phi_1}\delta\left(\frac{x}{\lambda z}, \frac{y}{\lambda z}\right)\right]^2 \quad (4)$$

From this formula, the intensity of the 0th (I0), 1st (I1), and 2nd (I2) order diffraction light is $$I_0 = \left(\frac{1}{\lambda z}\right)^2 \times \left[(e^{i2\pi \times \frac{(n+\Delta n) \times b}{\lambda}} - e^{i2\pi \times \frac{n \times b}{\lambda}})\frac{a}{d} + e^{i2\pi \times \frac{n \times b}{\lambda}}\right]^2 \quad (5)$$

$$I_1 = \left(\frac{1}{\lambda z}\right)^2 \times \left[(e^{i2\pi \times \frac{(n+\Delta n) \times b}{\lambda}} - e^{i2\pi \times \frac{n \times b}{\lambda}})\frac{a}{d} sinc\left(\frac{a}{d}\right)\right]^2 \quad (6)$$

and $$I_2 = \left(\frac{1}{\lambda z}\right)^2 \times \left[(e^{i2\pi \times \frac{(n+\Delta n) \times b}{\lambda}} - e^{i2\pi \times \frac{n \times b}{\lambda}})\frac{a}{d} sinc\left(\frac{2a}{d}\right)\right]^2 \quad (7)$$

By comparing the light intensities of $1^{st}$, $2^{nd}$ and $0^{th}$ diffraction orders, the refractive index change within the grating lines can be determined. FIG. 3 shows the ratio of intensity of the $1^{st}$ and $2^{nd}$ diffraction order to $0^{th}$ order of the grating in PV2526-164 is 0.1374 and 0.0842 respectively, and the corresponding refractive index change determined by the analysis is about 0.06. Using the same method, we determined the average refractive index change in RD1817 and HEMA B to be 0.05±0.0005 and 0.03±0.0005. Thus, it was demonstrated that the refractive index of a material can be modified by applying an ultrafast laser thereto.

Example 5

A femtosecond laser oscillator with a Kerr-lens modelocked Ti:Sapphire laser (MaiTai HP from Newport), generating pulses of 100 fs pulsewidth and 80 MHz repetition rate at a tunable wavelength range from 690 nm to 1040 nm was used in the following Examples. In the experiments, the average laser power at the focus of the objective was attenuated and adjusted by a variable attenuator, and was set below 160 mW (2 nJ pulse energy) to avoid gross optical damage in the hydrogel polymers. Three Newport VP-25XA linear servo stages with 100 nm resolution formed a 3D smooth scanning platform which was controlled and programmed by a computer. The focusing objective was a 60× 0.70NA Olympus LUCPlanFLN long-working-distance objective which could precisely correct the spherical aberration and create nearly diffraction-limited laser focal spot at different depths below the material surface.

During the laser pulse irradiation sequence, the optical, hydrogel polymeric materials were maintained within an aqueous environment in a sandwich structure between two coverslips, and mounted horizontally on the scanning platform. The femtosecond laser pulses were focused vertically inside the hydrogel samples through the focusing objective. Different horizontal scanning speeds from 0.4 μm/s to 4 mm/s were used with different polymeric hydrogels and different average laser power. A CCD camera was used to monitor the irradiation process and detect plasma illumination, which indicated the onset of laser-induced material breakdown. After laser irradiation, the materials were removed and observed under a calibrated Olympus BX51 microscope with different modes. The change in refractive index of the irradiated regions were measured either by grating experiments as described in L. Ding et al., in "*Large refractive index change in silicone-based and non-silicone-based hydrogel polymers induced by femtosecond laser micro-machining*," Opt. Express 2006, 14, 11901-11909, or by a calibrated differential interference contrast (DIC) mode microscope.

Example 5A to 5D

Optical, hydrogel polymeric materials comprising hydroxyethyl methacrylate (HEMA), methylmethacrylate (MMA), ethylene glycol dimethacrylate (EGDMA) and variable concentrations of fluorescein-methacrylate (Fluo-MA), were prepared and are summarized in Table 1. A master monomer batch containing HEMA (83.7 wt. %), MMA (13.7 wt. %), EGDMA (0.51 wt. %) and AIBN (0.1 wt. %) initiator was prepared. An appropriate amount of Fluor-MA was added to separate monomer preparations to provide monomer mixture with the stated wt. % of Fluor-MA listed in Table 1. The monomer mixtures were polymerized according to well known methods in the art and cured in the form of 700 µm-thick flat films.

The HEMA-based hydrogel polymers have a water content of about 28% by weight and an average refractive index of 1.44. An Ocean Optics HR4000 spectrometer was usually used to measure their transmission spectra.

TABLE 1

| | Ex. No. | | | | |
|---|---|---|---|---|---|
| | 5A | 5B | 5C | 5D | 5E |
| Fluor-MA | — | 0.0625 | 0.125 | 0.25 | 0.5 |

Figure 14:
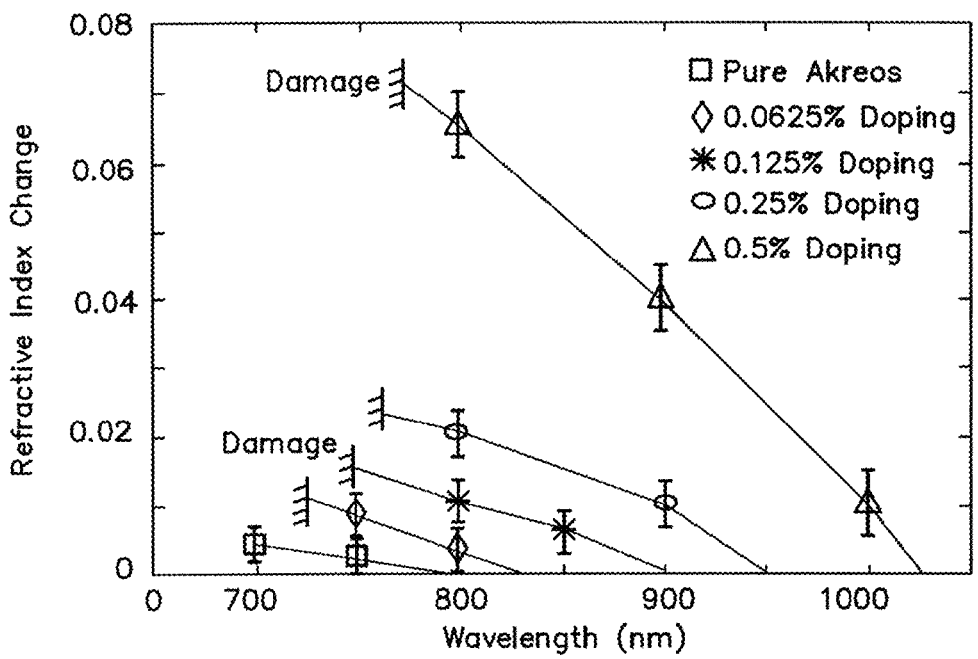
FIG. 14 is a plot of the measured change in refractive index at various wavelengths, an average pulse energy of 1.5 nJ and a scan rate of 1 mm/s for the hydrogel materials of Examples 5A and 5E.

FIG. 14 shows the transmission spectra of the non-photosensitized hydrogel material as well as the near identical hydrogel materials doped with different concentrations of Fluor-MA. As shown, the absorption peaks centered at about 350 nm to about 450 nm increased with an increase in the Fluor-MA concentration. Each of the Fluor-MA doped hydrogel materials remained transparent in the near infrared region though some scattering loss was observed at higher doping concentrations.

Figure 15:
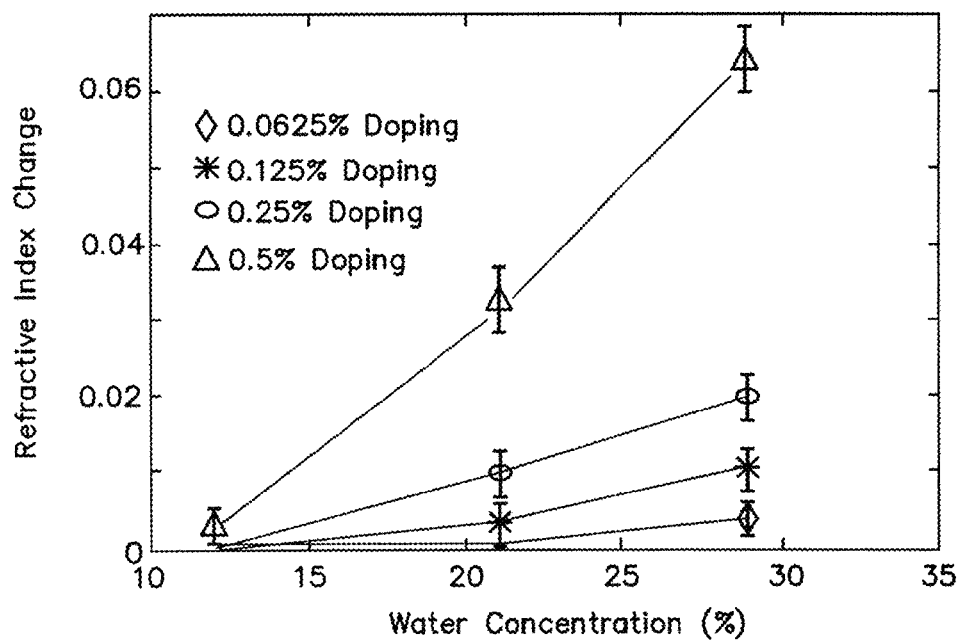
FIG. 15 is a plot of the measured change in refractive index for hydrogel materials with variable water content.

Each of the HEMA-based hydrogel materials were micromachined (irradiated) with femtosecond pulse sequence at 800 nm and 120 mW average power. Horizontal periodic gratings were typically written~100-150 µm beneath the top surface of the materials at different scanning speeds. The changes in refractive index with different scanning speeds were measured for each material and are shown in FIG. 15. The degree of change in refractive index decreased as the scanning speed increased. For example, the largest refractive index change in the non-doped material was about 0.03±0.005 at a scan speed of 3 µm/s. Carbon damage spots were observed in the non-doped material if the scanning speed was less than 2 µm/s. Also, the degree of change in refractive index decreased very quickly as the scanning speed increased. At a scanning speed greater than 10 µm/s, the changes in refractive index were too small to be measured in our experiments (<0.005).

In contrast, with the doped hydrogel materials, we needed to significantly increase the scanning speed to avoid optical damage (carbonization) of the materials, which we believe are induced by accumulated heat. For Example 5B with 0.0625% Fluo-MA, a scanning speed of at least 40 µm/s was required to avoid carbonized damage to the material. For Example 5E with 0.5% Fluo-MA one would observe small spot evidence of damage within the material even at a scanning speed of 500 µm/s. Also, trradiation of the Example 5E at a scanning speed of 600 µm/s, we measured a change in the refractive index of 0.085±0.005.

In general, the degree of change in the refractive index decreased as the Fluor-MA doping concentration decreased with a constant scan speed. For example, with a scanning speed of 1 mm/s, the measured change in refractive index for the 0.5% and 0.0625% Fluor-doped materials was 0.065±0.005 and 0.005±0.002, respectively. In fact, for the 0.5% Fluo-MA material, a change of refractive index of 0.025±0.005 was obtained at a scanning speed of 4 mm/s. These results indicate that nonlinear absorption within the hydrogel polymers could be greatly increased if Fluo-MA is copolymerized into the polymer network.

Large changes in refractive index could be observed at scanning speeds that are 1000× faster than the non-doped material. If the Fluor-MA concentration in the hydrogel materials of Example 5 was too high, i.e., greater than 3 wt %, we began to see aggregates (scattering centers) form within the hydrogel polymer network. Accordingly, for the HEMA-based materials of Example 5, the Fluor-MA concentration is from about 0.05 wt. % to about 2 wt. %, or from 0.1 wt. % to about 1.5 wt. %. To summarize, we have shown that as the concentration of the photosensitizer monomer, Fluor-MA, in the polymeric hydrogels increased, we observed a corresponding increase in the degree of change in refractive index within the focal volume even at significantly greater scan rates (FIG. 15).

Figure 16:
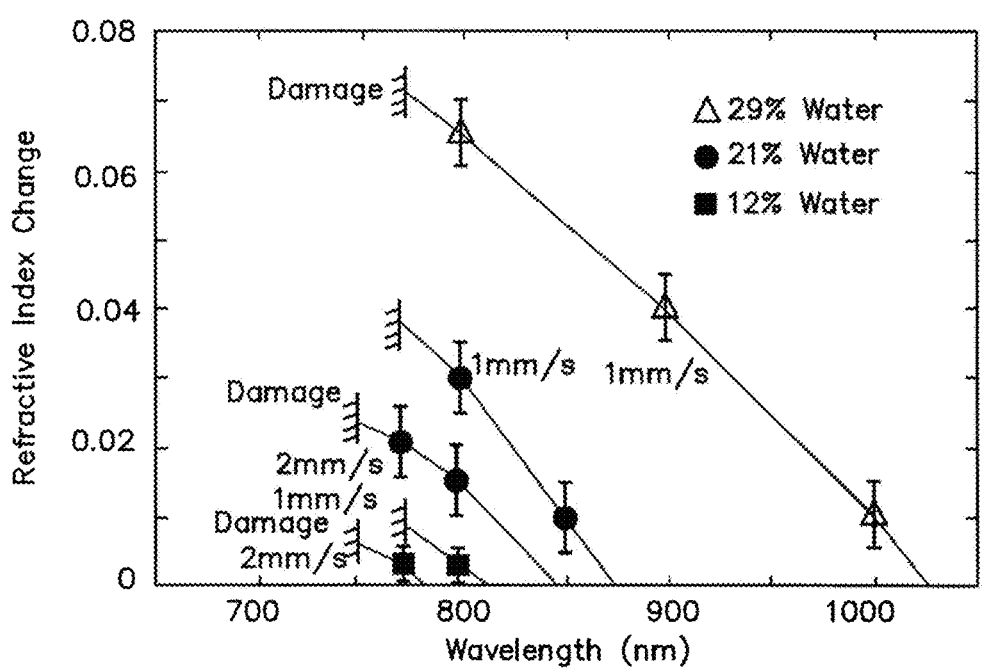
FIG. 16 is a plot of the measured change in refractive index at various wavelengths for hydrogel materials with variable water content.

FIGS. 16A and 16B summarizes our experimental investigations with Example 5A (non-doped) and Example 5E (0.5% Fluo-MA) using two different pulse energies: (a) 1.5 nJ (120 mW average power); and (b) 2 nJ (160 mW average power). For both hydrogel materials, the degree of change in refractive index decreased as the femtosecond laser was tuned to operate at a longer wavelength at a constant scan rate. For Example 5A, the degree of change in refractive index was less than 0.01 for all laser wavelengths. An attempt to increase the pulse energy or decrease the scan rate resulted only in optical damage. For all wavelengths longer than 850 nm, no change in refractive index was observed in Example 5A at either pulse energy even if the scan rate was greater than 100 µm/s. Higher pulse energies and slower scan rates were also tested in this wavelength region, but only optical damage with no change in refractive index was observed. In contrast, significantly large changes in refractive index was measured in Example 5E. In addition, because of the nonlinear absorption enhancement provided by the photosensitized material, material damage was observed at the shorter wavelengths. For example, even with a scan rate of 2 mm/s and a pulse energy of 1.5 nJ, some optical damage is observed at wavelengths less than 775 nm.

The irradiation of Example 5E at longer wavelengths (greater than 800 nm) did result in relatively large changes in refractive index within the focal volume of the material. FIG. 16A shows that one could achieve a change in refractive index of 0.06 in the focal volume of the material with a scan rate of 0.5 mm/s at a wavelength of 900 nm. Also, by increasing the average laser pulse energy from 1.5 nJ to 2.0 nJ one could achieve even greater changes in refractive index, but some optical damage was observed. A comparison of the data and plots of FIG. 16A and FIG. 16B, indicates that an increase in pulse energy from 1.5 nJ to 2 nJ results in optical damage at a wavelength of 900 nm and the scan rate of 0.5 mm/s. Also, if the scan rate is increased to 1 mm/s, we observed very small changes in refractive index (on the order of about 0.005) was observed.

To further investigate the wavelength dependence with respect to changes in refractive index within the focal volume, Examples 5A to 5E were irradiated over a wavelength range from 700 nm to 1000 nm at variable scan rates and an average pulse energy of 1.5 nJ. For each hydrogel material, the degree of change in refractive index decreased with laser wavelength and increased with the Fluor-MA concentration. FIG. 17 shows the data and plots of Example 5E at a scan rate of 1 mm/s. The data of FIG. 17 is very helpful because it suggests a window of operating parameters in which one can form the refractive structures in the hydrogel materials, and yet, remain a safe working distance from forming any significant optical damage (scattering features) in the materials. For Example 5D and 5E, irradiation at 850 nm to 900 nm provides a safe working distance from optical damage, and yet provides a significant appreciable change in refractive index, i.e., from 0.01 to 0.04, respectively, at the given scan rate and average laser power—one can even see an appreciable change in refractive index at 950 nm for Example 5E.

As already stated, we believe that the presence of water within the polymer matrix, as in the case of a hydrated hydrogel material, plays a critical part in forming the observed changes in refractive index within the focal volume. Accordingly, we investigated the effect of water concentration on the degree of change in refractive index in the hydrogel materials of Examples 5B to 5E as well as those of similar composition, but with reduced water content. A master monomer batch containing HEMA (68.6 wt. %), MMA (28.9 wt. %), EGDMA (0.51 wt. %) and AIBN (0.1 wt. %) initiator was prepared. An appropriate amount of Fluor-MA was added to separate monomer preparations to provide monomer mixture with the stated wt. % of Fluor-MA listed in Table 2. The monomer mixtures were polymerized according to well known methods in the art and cured in the form of 700 μm-thick flat films. The hydrogel polymers of Example 6 have a 21% water content.

Likewise, the hydrogel materials of Example 7 were prepared from a master monomer batch containing HEMA (49.0 wt. %), MMA (48.4 wt. %), EGDMA (0.51 wt. %) and AIBN (0.1 wt. %) initiator was prepared. An appropriate amount of Fluor-MA was added to separate monomer preparations to provide monomer mixture with the stated wt. % of Fluor-MA listed in Table 2. The monomer mixtures were polymerized according to well known methods in the art and cured in the form of 700 μm-thick flat films. The hydrogel polymers of Example 7 have a 12% water content.

TABLE 2

| | Ex. No. | | | |
| --- | --- | --- | --- | --- |
| | 6A | 6B | 6C | 6D |
| Fluor-MA | 0.0625 | 0.125 | 0.25 | 0.5 |

TABLE 3

| | Ex. No. | | | |
| --- | --- | --- | --- | --- |
| | 7A | 7B | 7C | 7D |
| Fluor-MA | 0.0625 | 0.125 | 0.25 | 0.5 |

As indicated, each set of materials of Examples 5 to 7 have varying concentrations of the photosensitizer, Fluo-MA. FIG. 18 shows the resulting change in refractive index in these hydrogel materials at an irradiation wavelength of 800 nm, 1.5 nJ average pulse energy and a scan rate of 1 mm/s. Again, the data and plots provide very important information. As shown, the degree of change in refractive index decreased as the water concentration decreased in all the photosensitized hydrogel materials. We believe the localized water concentration of the hydrogel affects the thermodynamic properties such as specific heat, heat capacity, etc. as well as the material density of the materials. The largest change in refractive index is obtained in the hydrogels of Example 5, which have largest water content of about 28%. More importantly, the hydrogels with relatively larger water content provide the largest safe working distance to form the refractive structures without optical damage to the material.

We also investigated the wavelength dependence of the hydrogel materials of Example 5E, Example 6D and Example 7D, each with 0.5% Fluor-MA, but with the different water contents, see FIG. 19. Interestingly, a relatively large change in refractive index (greater than 0.02) without any optical damage was observed only in Example 5E at an average pulse energy of 1.5 nJ. One must note, however that we also used a relatively fast scan rate of 1 mm/s in this investigation. As indicated, if the laser wavelength was less than about 750 nm, we observed only optical damage. If the laser pulses were operating at a wavelength greater than 800 nm, no change in refractive index is observed and optical damage is observed in the hydrogel materials of Example 7 (12% water content). For the hydrogel materials of Example 6 (21% water content), a change in refractive index of 0.01 is observed without optical damage if the irradiation wavelength is about 875 nm.

Collectively, our investigation suggests the optimal irradiation conditions for forming the described refractive structure in optical, hydrogel polymeric materials.

We claim:

1. An optical device comprising an optical, hydrogel polymeric material with irradiated regions that define refractive structures, wherein the irradiated regions are characterized by a positive change in refractive index and exhibit little or no scattering loss, and the optical, polymeric material comprises a photosensitizer to enhance the photoefficiency of two photon absorption by the polymeric material to form the refractive structures, wherein the photosensitizer permits one to irradiate the regions at a given average laser power using a scan rate that is at least fifty times greater than a scan rate without the photosensitizer in the material, or at a given scan rate that permits one to set an average power of the laser to a value that is at least two times less than an average laser power without the photosensitizer in the material, yet provide a similar positive change in refractive index within the irradiated regions, and wherein the optical, hydrogel polymeric material further includes at least three monomeric components: a first monomeric component is present in an amount of at least 60% by weight, and its homopolymer will have a refractive index of at least 1.50; a second monomeric component is present in an amount from 3% to 20% by weight, and a hydrophilic component present in an amount from 2% to 30% by weight.

2. The optical device of claim 1 wherein the irradiated regions of the optical material are defined within a two-dimensional plane or by a three-dimensional structure.

3. The optical device of claim 2 wherein the optical polymeric material is a component of an intraocular lens.

4. The optical device of claim 3 wherein the optical polymeric material is prepared from one or more (meth)acrylate monomers selected from the group consisting of 2-hydroxymethyl(meth)acrylate, 2-phenylethyl(meth)acrylate, methyl(meth)acrylate and 3-phenylpropyl(meth)acrylate.

5. The optical device of claim 3 wherein the positive change in refractive index is variable within the focal volume to provide a extended depth of field to the lens relative to a base lens prior to irradiating regions with the laser.

6. An optical device comprising an optical, hydrogel polymeric material that includes a photosensitizer to facilitate the formation of refractive structures with a laser by irradiating regions of the polymeric material, the laser light having a wavelength from 650 nm to 950 nm and a pulse energy from 0.05 nJ to 100 nJ, wherein the refractive structures are characterized by a positive change in refractive index of from 0.01 to 0.06 and exhibit little or no scattering loss, relative to the optical hydrogel material outside the irradiated regions, said optical, hydrogel polymeric material having a water content of at least 15%, and wherein the optical, hydrogel polymeric material further includes at least three monomeric components: a first monomeric component is present in an amount of at least 60% by weight, and its homopolymer will have a refractive index of at least 1.50; a second monomeric component is present in an amount from 3% to 20% by weight, and a hydrophilic component present in an amount from 2% to 30% by weight.

7. The optical device of claim 6 wherein the optical, hydrogel polymeric material is a component of an intraocular lens.

8. The optical device of claim 6 wherein the optical, hydrogel polymeric material is a component of a corneal inlay.

9. The optical device of claim 7 wherein the refractive structures take the form of positive or negative lens elements.

10. The optical device of claim 9 wherein the positive or negative lens elements are disposed in a volume of the polymeric material that is within 300 μm from the anterior surface of the intraocular lens.

11. The optical device of claim 6 wherein the photosensitizer has a multi-photon cross section of at least $0.01 \times 10^{-50}$ cm$^4$ s.

12. The optical device of claim 6 wherein the photosensitizer is a polymerizable monomer having a chromophore functional moiety.

13. The optical device of claim 1 wherein the photosensitizer has a multi-photon cross section of at least $0.01 \times 10^{-50}$ cm$^4$ s.

14. The optical device of claim 1 wherein the photosensitizer is a polymerizable monomer having a chromophore functional moiety.

15. The optical device of claim 6 wherein the optical, hydrogel polymeric material comprises about 80% by weight HEMA.

16. The optical device of claim 1 wherein the optical, hydrogel polymeric material comprises about 80% by weight HEMA.

* * * * *